US011147921B2

(12) United States Patent
Desborough et al.

(10) Patent No.: US 11,147,921 B2
(45) Date of Patent: Oct. 19, 2021

(54) ADJUSTING INSULIN DELIVERY RATES

(71) Applicant: Bigfoot Biomedical, Inc., Milpitas, CA (US)

(72) Inventors: Lane Desborough, Thousand Oaks, CA (US); Bryan Mazlish, Palo Alto, CA (US)

(73) Assignee: Bigfoot Biomedical, Inc., Milpitas, CA (US)

( * ) Notice: Subject to any disclaimer, the term of this patent is extended or adjusted under 35 U.S.C. 154(b) by 271 days.

(21) Appl. No.: 16/393,831

(22) Filed: Apr. 24, 2019

(65) Prior Publication Data
US 2019/0247578 A1 Aug. 15, 2019

Related U.S. Application Data

(63) Continuation of application No. 15/406,313, filed on Jan. 13, 2017, now Pat. No. 10,307,538.
(Continued)

(51) Int. Cl.
*A61M 5/172* (2006.01)
*G16H 20/17* (2018.01)
(Continued)

(52) U.S. Cl.
CPC ....... *A61M 5/1723* (2013.01); *A61B 5/14532* (2013.01); *A61B 5/4839* (2013.01);
(Continued)

(58) Field of Classification Search
None
See application file for complete search history.

(56) References Cited

U.S. PATENT DOCUMENTS 4,464,170 A 8/1984 Clemens et al.
5,733,259 A 3/1998 Valcke et al.
(Continued)

FOREIGN PATENT DOCUMENTS

AU 2015200829 A1 3/2015
CN 101010676 A 8/2007
(Continued)

OTHER PUBLICATIONS

Written Opinion of the International Searching Authority, as issued in connection with the International Patent Application No. PCT/US17/34012 dated Aug. 17, 2017.
(Continued)

*Primary Examiner* — Jenna Zhang
(74) *Attorney, Agent, or Firm* — TraskBritt

(57) ABSTRACT

A method may include generating a first plurality of insulin delivery profiles that include a first series of insulin delivery actions spanning a first time interval, projecting a first plurality of future blood glucose values for each profile of the first plurality of profiles using up-to-date blood glucose levels, selecting one of the first plurality of profiles based upon comparing future blood glucose values for each profile and target blood glucose levels, delivering insulin for a second time interval that corresponds to a first action of the first profile, generating a second plurality of insulin delivery profiles for a third time interval, projecting a second plurality of future blood glucose values for each profile of the second plurality of profiles for the third time interval, and delivering a second dose of insulin for a fourth time interval shorter than the third time interval.

20 Claims, 11 Drawing Sheets

Related U.S. Application Data

(60) Provisional application No. 62/278,978, filed on Jan. 14, 2016, provisional application No. 62/340,470, filed on May 23, 2016.

(51) Int. Cl.

| | | |
|---|---|---|
| *A61M 5/142* | (2006.01) | |
| *G16H 40/67* | (2018.01) | |
| *G16H 40/60* | (2018.01) | |
| *A61B 5/145* | (2006.01) | |
| *A61B 5/00* | (2006.01) | |
| *A61M 5/145* | (2006.01) | |
| *G16H 40/40* | (2018.01) | |
| *G16H 10/60* | (2018.01) | |
| *G16H 50/30* | (2018.01) | |

(52) U.S. Cl.
CPC ............ *A61M 5/142* (2013.01); *A61M 5/145* (2013.01); *A61M 5/14244* (2013.01); *A61M 5/14248* (2013.01); *G16H 20/17* (2018.01); *G16H 40/60* (2018.01); *G16H 40/67* (2018.01); *A61B 2562/0295* (2013.01); *A61M 2005/14208* (2013.01); *A61M 2205/3303* (2013.01); *A61M 2205/3553* (2013.01); *A61M 2205/3561* (2013.01); *A61M 2205/3569* (2013.01); *A61M 2205/3584* (2013.01); *A61M 2205/502* (2013.01); *A61M 2205/52* (2013.01); *A61M 2230/005* (2013.01); *A61M 2230/201* (2013.01); *G16H 10/60* (2018.01); *G16H 40/40* (2018.01); *G16H 50/30* (2018.01)

(56) References Cited

U.S. PATENT DOCUMENTS

| | | | |
|---|---|---|---|
| 6,379,301 | B1 | 4/2002 | Worthington et al. |
| 6,544,212 | B2 | 4/2003 | Galley et al. |
| 6,551,276 | B1 | 4/2003 | Mann et al. |
| 6,554,798 | B1 | 4/2003 | Mann et al. |
| 6,558,351 | B1 | 5/2003 | Steil et al. |
| 6,599,281 | B1 | 7/2003 | Struys et al. |
| 6,605,072 | B2 | 8/2003 | Struys et al. |
| 6,648,821 | B2 | 11/2003 | Lebel et al. |
| 6,740,072 | B2 | 5/2004 | Starkweather et al. |
| 6,799,149 | B2 | 9/2004 | Hartlaub |
| 6,827,702 | B2 | 12/2004 | Lebel et al. |
| 6,872,200 | B2 | 3/2005 | Mann et al. |
| 6,873,268 | B2 | 3/2005 | Lebel et al. |
| 6,936,029 | B2 | 8/2005 | Mann et al. |
| 6,979,326 | B2 | 12/2005 | Mann et al. |
| 6,997,920 | B2 | 2/2006 | Mann et al. |
| 7,025,743 | B2 | 4/2006 | Mann et al. |
| 7,060,059 | B2 | 6/2006 | Keith et al. |
| 7,066,910 | B2 | 6/2006 | Bauhahn et al. |
| 7,109,878 | B2 | 9/2006 | Mann et al. |
| 7,133,329 | B2 | 11/2006 | Skyggebjerg et al. |
| 7,179,226 | B2 | 2/2007 | Crothall et al. |
| 7,204,823 | B2 | 4/2007 | Estes et al. |
| 7,220,240 | B2 | 5/2007 | Struys et al. |
| 7,267,665 | B2 | 9/2007 | Steil et al. |
| 7,354,420 | B2 | 4/2008 | Steil et al. |
| 7,402,153 | B2 | 7/2008 | Steil et al. |
| 7,404,796 | B2 | 7/2008 | Ginsberg |
| 7,491,187 | B2 | 2/2009 | Van et al. |
| 7,547,281 | B2 | 6/2009 | Hayes et al. |
| 7,569,030 | B2 | 8/2009 | Lebel et al. |
| 7,651,845 | B2 | 1/2010 | Doyle et al. |
| 7,704,226 | B2 | 4/2010 | Mueller et al. |
| 7,734,323 | B2 | 6/2010 | Blomquist et al. |
| 7,766,829 | B2 | 8/2010 | Sloan et al. |
| 7,785,313 | B2 | 8/2010 | Mastrototaro |
| 7,806,853 | B2 | 10/2010 | Wittmann et al. |
| 7,806,854 | B2 | 10/2010 | Damiano et al. |
| 7,815,602 | B2 | 10/2010 | Mann et al. |
| 7,819,843 | B2 | 10/2010 | Mann et al. |
| 7,850,641 | B2 | 12/2010 | Lebel et al. |
| 7,967,812 | B2 | 6/2011 | Jasperson et al. |
| 7,976,492 | B2 | 7/2011 | Brauker et al. |
| 8,062,249 | B2 | 11/2011 | Wilinska et al. |
| 8,088,098 | B2 | 1/2012 | Yodfat et al. |
| 8,105,268 | B2 | 1/2012 | Lebel et al. |
| 8,152,789 | B2 | 4/2012 | Starkweather et al. |
| 8,206,350 | B2 | 6/2012 | Mann et al. |
| 8,208,984 | B2 | 6/2012 | Blomquist et al. |
| 8,226,556 | B2 | 7/2012 | Hayes et al. |
| 8,267,893 | B2 | 9/2012 | Moberg et al. |
| 8,273,052 | B2 | 9/2012 | Damiano et al. |
| 8,352,011 | B2 | 1/2013 | Van et al. |
| 8,417,311 | B2 | 4/2013 | Rule |
| 8,439,834 | B2 | 5/2013 | Schmelzeisen-Redeker et al. |
| 8,439,897 | B2 | 5/2013 | Yodfat et al. |
| 8,454,576 | B2 | 6/2013 | Mastrototaro et al. |
| 8,460,231 | B2 | 6/2013 | Brauker et al. |
| 8,480,655 | B2 | 7/2013 | Jasperson et al. |
| 8,548,544 | B2 | 10/2013 | Kircher et al. |
| 8,551,045 | B2 | 10/2013 | Sie et al. |
| 8,560,082 | B2 | 10/2013 | Wei |
| 8,560,131 | B2 | 10/2013 | Haueter et al. |
| 8,562,587 | B2 | 10/2013 | Kovatchev et al. |
| 8,579,879 | B2 | 11/2013 | Palerm et al. |
| 8,585,591 | B2 | 11/2013 | Sloan et al. |
| 8,585,637 | B2 | 11/2013 | Wilinska et al. |
| 8,585,638 | B2 | 11/2013 | Blomquist |
| 8,615,366 | B2 | 12/2013 | Galley et al. |
| 8,694,115 | B2 | 4/2014 | Goetz et al. |
| 8,706,691 | B2 | 4/2014 | McDaniel et al. |
| 8,718,949 | B2 | 5/2014 | Blomquist et al. |
| 8,721,585 | B2 | 5/2014 | Brauker et al. |
| 8,727,982 | B2 | 5/2014 | Jennewine |
| 8,734,428 | B2 | 5/2014 | Blomquist |
| 8,747,315 | B2 | 6/2014 | Brauker et al. |
| 8,756,043 | B2 | 6/2014 | Albisser et al. |
| 8,768,673 | B2 | 7/2014 | Albisser et al. |
| 8,777,896 | B2 | 7/2014 | Starkweather et al. |
| 8,784,369 | B2 | 7/2014 | Starkweather et al. |
| 8,784,370 | B2 | 7/2014 | Lebel et al. |
| 8,795,224 | B2 | 8/2014 | Starkweather et al. |
| 8,876,755 | B2 | 11/2014 | Taub et al. |
| 8,945,094 | B2 | 2/2015 | Nordh |
| 8,977,504 | B2 | 3/2015 | Hovorka |
| 8,992,475 | B2 | 3/2015 | Mann et al. |
| 9,056,165 | B2 | 6/2015 | Steil et al. |
| 9,320,471 | B2 | 4/2016 | Hayes et al. |
| 9,333,298 | B2 | 5/2016 | Kim et al. |
| 9,415,157 | B2 | 8/2016 | Mann et al. |
| 9,474,855 | B2 | 10/2016 | McCann et al. |
| 9,480,796 | B2 | 11/2016 | Starkweather et al. |
| 9,486,172 | B2 | 11/2016 | Cobelli et al. |
| 9,486,578 | B2 | 11/2016 | Finan et al. |
| 10,102,344 | B2 | 10/2018 | Rees et al. |
| 10,195,343 | B2 | 2/2019 | Kamen et al. |
| 10,307,538 | B2 | 6/2019 | Desborough et al. |
| 10,391,242 | B2 | 8/2019 | Agrawal et al. |
| 10,500,334 | B2 | 12/2019 | Mazlish et al. |
| 10,583,250 | B2 | 3/2020 | Mazlish et al. |
| 10,610,644 | B2 | 4/2020 | Mazlish et al. |
| 2003/0060765 | A1 | 3/2003 | Campbell et al. |
| 2003/0114836 | A1 | 6/2003 | Estes et al. |
| 2003/0181852 | A1 | 9/2003 | Mann et al. |
| 2003/0187525 | A1 | 10/2003 | Mann et al. |
| 2003/0191431 | A1 | 10/2003 | Mann et al. |
| 2003/0195462 | A1 | 10/2003 | Mann et al. |
| 2003/0212364 | A1 | 11/2003 | Mann et al. |
| 2005/0171513 | A1 | 8/2005 | Mann et al. |
| 2006/0253067 | A1 | 11/2006 | Staib et al. |
| 2008/0033357 | A1 | 2/2008 | Mann et al. |
| 2008/0097289 | A1 | 4/2008 | Steil et al. |
| 2008/0147004 | A1 | 6/2008 | Mann et al. |
| 2008/0147050 | A1 | 6/2008 | Mann et al. |
| 2008/0183060 | A1 | 7/2008 | Steil et al. |
| 2008/0208113 | A1 | 8/2008 | Damiano et al. |
| 2008/0269714 | A1 | 10/2008 | Mastrototaro et al. |

(56) References Cited

U.S. PATENT DOCUMENTS

| | | |
|---|---|---|
| 2008/0269723 A1 | 10/2008 | Mastrototaro et al. |
| 2008/0319384 A1 | 12/2008 | Yodfat et al. |
| 2009/0149728 A1 | 6/2009 | Van et al. |
| 2009/0164239 A1 | 6/2009 | Hayter et al. |
| 2009/0164251 A1 | 6/2009 | Hayter |
| 2010/0049164 A1 | 2/2010 | Estes |
| 2010/0082167 A1 | 4/2010 | Haueter et al. |
| 2010/0125241 A1 | 5/2010 | Prud et al. |
| 2010/0137788 A1 | 6/2010 | Braithwaite et al. |
| 2010/0138197 A1 | 6/2010 | Sher |
| 2010/0249561 A1 | 9/2010 | Patek et al. |
| 2010/0256466 A1 | 10/2010 | Shekalim et al. |
| 2010/0262117 A1 | 10/2010 | Magni et al. |
| 2010/0298765 A1 | 11/2010 | Budiman et al. |
| 2011/0015511 A1 | 1/2011 | Bousamra et al. |
| 2011/0208156 A1 | 8/2011 | Doyle et al. |
| 2012/0059351 A1 | 3/2012 | Nordh |
| 2012/0123234 A1 | 5/2012 | Atlas et al. |
| 2012/0172694 A1 | 7/2012 | Desborough et al. |
| 2012/0227737 A1 | 9/2012 | Mastrototaro et al. |
| 2012/0245556 A1 | 9/2012 | Kovatchev et al. |
| 2012/0246106 A1 | 9/2012 | Atlas et al. |
| 2012/0246406 A1 | 9/2012 | Bell et al. |
| 2013/0102867 A1 | 4/2013 | Desborough et al. |
| 2013/0231642 A1 | 9/2013 | Doyle et al. |
| 2013/0245547 A1 | 9/2013 | El-Khatib et al. |
| 2013/0338629 A1 | 12/2013 | Agrawal et al. |
| 2013/0338630 A1 | 12/2013 | Agrawal et al. |
| 2013/0345663 A1 | 12/2013 | Agrawal et al. |
| 2014/0005633 A1 | 1/2014 | Finan |
| 2014/0066884 A1 | 3/2014 | Keenan et al. |
| 2014/0066887 A1 | 3/2014 | Mastrototaro et al. |
| 2014/0066888 A1 | 3/2014 | Parikh et al. |
| 2014/0066889 A1* | 3/2014 | Grosman ............ A61M 5/1723 604/504 |
| 2014/0180240 A1* | 6/2014 | Finan ................ A61M 5/1723 604/504 |
| 2014/0188072 A1 | 7/2014 | Rinehart et al. |
| 2014/0276553 A1 | 9/2014 | Rosinko et al. |
| 2014/0276554 A1 | 9/2014 | Finan et al. |
| 2014/0276555 A1* | 9/2014 | Morales ............ A61M 5/1782 604/504 |
| 2014/0309615 A1 | 10/2014 | Mazlish |
| 2014/0350369 A1 | 11/2014 | Budiman et al. |
| 2015/0045767 A1 | 2/2015 | Kamen et al. |
| 2015/0073337 A1 | 3/2015 | Saint et al. |
| 2015/0164343 A1 | 6/2015 | Huang et al. |
| 2015/0165117 A1 | 6/2015 | Palerm et al. |
| 2015/0238694 A1 | 8/2015 | Steil et al. |
| 2015/0289823 A1 | 10/2015 | Rack-Gomer et al. |
| 2015/0314062 A1 | 11/2015 | Blomquist et al. |
| 2015/0328402 A1 | 11/2015 | Nogueira et al. |
| 2016/0030669 A1 | 2/2016 | Harris et al. |
| 2016/0038673 A1 | 2/2016 | Morales |
| 2016/0082187 A1 | 3/2016 | Schaible et al. |
| 2016/0082188 A1 | 3/2016 | Blomquist et al. |
| 2016/0158438 A1 | 6/2016 | Monirabbasi et al. |
| 2016/0162662 A1 | 6/2016 | Monirabbasi et al. |
| 2016/0213841 A1 | 7/2016 | Geismar et al. |
| 2016/0256629 A1 | 9/2016 | Grosman et al. |
| 2016/0317743 A1 | 11/2016 | Estes |
| 2017/0049386 A1 | 2/2017 | Abraham et al. |
| 2017/0182248 A1 | 6/2017 | Rosinko |
| 2017/0203038 A1 | 7/2017 | Desborough et al. |
| 2017/0232195 A1 | 8/2017 | Desborough et al. |
| 2017/0332952 A1 | 11/2017 | Desborough et al. |
| 2018/0200434 A1 | 7/2018 | Mazlish et al. |
| 2018/0200436 A1 | 7/2018 | Mazlish et al. |
| 2018/0200440 A1 | 7/2018 | Mazlish et al. |
| 2018/0200441 A1 | 7/2018 | Desborough et al. |

FOREIGN PATENT DOCUMENTS

| | | |
|---|---|---|
| CN | 102500013 A | 6/2012 |
| CN | 102596307 A | 7/2012 |
| CN | 103400028 A | 11/2013 |
| CN | 103418053 A | 12/2013 |
| CN | 103907116 A | 7/2014 |
| CN | 104769595 A | 7/2015 |
| CN | 104837517 A | 8/2015 |
| CN | 105452866 A | 3/2016 |
| EP | 2967450 | 1/2016 |
| JP | 2008-545454 A | 12/2008 |
| JP | 2010-531678 A | 9/2010 |
| WO | 2006/021430 A2 | 3/2006 |
| WO | 2006/124716 A3 | 3/2007 |
| WO | 2008/057384 A3 | 9/2008 |
| WO | 2008/157780 A1 | 12/2008 |
| WO | 2009/146119 A2 | 12/2009 |
| WO | 2010/089307 A1 | 8/2010 |
| WO | 2011/030343 A1 | 3/2011 |
| WO | 2012/006208 A2 | 1/2012 |
| WO | 2014/035672 A2 | 3/2014 |
| WO | 2014/149535 A1 | 9/2014 |
| WO | 2015/187738 A1 | 12/2015 |
| WO | 2017/027459 A1 | 2/2017 |
| WO | 2017/124006 A1 | 7/2017 |

OTHER PUBLICATIONS

Written Opinion of the International Searching Authority, as issued in connection with the International Patent Application No. PCT/US17/13521, dated May 24, 2017, 12 pgs.

Search Report received in International Application No. PCT/US17/34012, dated Aug. 17, 2017.

Samuel Vozeh and Jean-Louis Steimer, Feedback Control Methods for Drug Dosage Optimisation, Concepts, Classification and Clinical Application, Clinical Pharmacokinetics, 10(6), pp. 457-476, Nov.-Dec. 1985.

Michele Schiavon, Chiara Dalla Man, Yogish C. Kudva, Ananda Basu, and Claudio Cobelli, Quantitative Estimation of Insulin Sensitivity in Type 1 Diabetic Subjects Wearing a Sensor-Augmented Insulin Pump, Diabetes Care, vol. 37, pp. 1216-1223, May 2014.

International Search Report and Written Opinion, as issued in connection with International Patent Application No. PCT/US17/13521, dated May 24, 2017, 5 pgs.

Fischer et al., In Vivo Comparison of Different Algorithms for the Artificial Beta-Cell, Artificial Organs, 9(2), International Society for Artificial Organs, May 1985, New York.

Extended European Search Report, European Application No. 18178057, dated Jan. 2, 2019, 7 pages.

European Supplementary Search Report for European Application No. 17739083.8, dated Jan. 2, 2019, 7 pages.

European Search Report and Search Opinion Received for EP Application No. 18178056, dated Jan. 3, 2019, 8 pages.

Dassau and Associates, 12-Week 24/7 Ambulatory Artificial Pancreas With Weekly Adaptation of Insulin Delivery Settings: Effect on Hemoglobin A1C and Hypoglycemia, Diabetes Care, Oct. 13, 2017.

David A. Copp, Ravi Gondhalekar, and Joao P. Hespanha, Simultaneous Model Predictive Control and Moving Horizon Estimation for Blood Glucose Regulation in Type 1 Diabetes, Optimal Control Applications and Methods, Wiley InterScience, DOI: 10.1002/oca, pp. 1-15, Oct. 2016.

Dunn et al. Development of the Likelihood of Low Glucose (LLG) Algorithm for Evaluating Risk of Hypoglycemia: A New Approach for Using Continuous Glucose Data to Guide Therapeutic Decision Making. Journal of Diabetes and Science Technology. 2014, vol. 8, No. 4, pp. 720-730 (Year: 2014).

E. Salzsieder, G. Albrecht, E. Jutzi, and U. Fischer, Estimation of Individually Adapted Control Parameters or an Artificial Beta Cell, Biomedica Biochimica Acta. 43(5) pp. 585-596, May 1984.

European search report dated Jan 3, 2019 for EP Application No. 18178056.

(56) References Cited

OTHER PUBLICATIONS

Guy A. Dumont, Feedback Control for Clinicians, Springer Science+Media, Apr. 12, 2013, New York.

* cited by examiner

ADJUSTING INSULIN DELIVERY RATES

CROSS-REFERENCE TO RELATED APPLICATIONS

This application is a continuation of U.S. patent application Ser. No. 15/406,313, filed Jan. 13, 2017, now U.S. Pat. No. 10,307,538, issued on Jun. 4, 2019 the disclosure of which is hereby incorporated herein in its entirety by this reference. A claim for benefit of priority to the Jan. 14, 2016 filing date of the U.S. Patent Provisional Application No. 62/278,978, titled "SYSTEMS AND METHODS FOR CHANGING TARGET GLUCOSE VALUES IN DIABETES MANAGEMENT SYSTEM" (the '978 Provisional Application), and the May 23, 2016 filing date of the U.S. Patent Provisional Application No. 62/340,470, titled "SYSTEMS AND METHODS FOR ADJUSTING INSULIN DELIVERY RATES" (the '470 Provisional Application), is hereby made pursuant to 35 U.S.C. § 119(e). The entire disclosures and contents of the '978 Provisional Application and the '470 Provisional Application are hereby incorporated herein in their entirety by this reference.

FIELD

This document relates to adjusting insulin delivery rates.

BACKGROUND

Diabetes mellitus is a chronic metabolic disorder caused by an inability of a person's pancreas to produce sufficient amounts of the hormone, insulin, such that the person's metabolism is unable to provide for the proper absorption of sugar and starch. This failure leads to hyperglycemia, i.e., the presence of an excessive amount of glucose within the blood plasma. Persistent hyperglycemia has been associated with a variety of serious symptoms and life threatening long-term complications such as dehydration, ketoacidosis, diabetic coma, cardiovascular diseases, chronic renal failure, retinal damage and nerve damages with the risk of amputation of extremities. Because healing is not yet possible, a permanent therapy is necessary that provides constant glycemic control in order to constantly maintain the level of blood glucose within normal limits. Such glycemic control is achieved by regularly supplying external drugs to the body of the patient to thereby reduce the elevated levels of blood glucose.

Historically, diabetes is treated with multiple, daily injections of rapid and long acting insulin via a hypodermic syringe. One or two injections per day of a long acting insulin is administered to provide a basal level of insulin and additional injections of a rapidly acting insulin is administered before or with each meal in an amount proportional to the size of the meal. Insulin therapy can also be administered using an insulin pump that provides periodic or continuous release of the rapidly acting insulin to provide for a basal level of insulin and larger doses of that same insulin at the time of meals. Insulin pumps allow for the delivery of insulin in a manner that bears greater similarity to the naturally occurring physiological processes and can be controlled to follow standard or individually modified protocols to give the patient better glycemic control. In some circumstances, an insulin pump device can store (via input from a clinician or a user) a number of settings (e.g., dosage parameters or other settings) that are customized by the physician for the particular user.

People with diabetes, their caregivers, and their health care providers (HCPs) bear a great deal of cognitive burden in managing intensive medicine therapy. Delivering the correct amount of the medicine at the correct time is an extremely challenging endeavor. Such delivery requires the patient to make dosing determinations multiple times per day and also requires a combination of the patient and the HCP to recalibrate the therapeutic parameters of the therapy on an episodic time frame that varies from individual to individual, and within individuals based on age and/or behavior (e.g., change in exercise, change in diet).

In light of the many deficiencies and problems associated with current systems and methods for maintaining proper glycemic control, enormous resources have been put into finding better solutions. A number of new technologies promise to mitigate some of the cognitive burden that intensive insulin therapy now requires. Developing workable solutions to the problem that are simple, safe, reliable and able to gain regulatory approval has, however, proved to be elusive. For years, researchers have contemplated coupling a continuous glucose monitoring system with an insulin delivery device to provide an "artificial pancreas" to assist people living with diabetes. Their efforts have yet to result in a commercial product. What has been needed is a system and method that provides a level of automatic control of drug delivery devices for improved medicine delivery and glycemic control that is simple, safe, and reliable in a real world setting.

SUMMARY

Methods and systems provided herein simplify the delivery of basal insulin, which can reduce the cognitive burden for managing diabetes for a user (e.g., a patient, caretaker, or clinician).

In one or more embodiments, the present disclosure may include a method that includes generating a first plurality of insulin delivery profiles. Each of the first plurality of insulin delivery profiles may include a first series of insulin delivery actions spanning a first time interval. The method may also include projecting a first plurality of future blood glucose values for each insulin delivery profile of the first plurality of insulin delivery profiles for a plurality of times spanning the first time interval. Each projected future blood glucose value may be projected using at least one up-to-date blood glucose level for a person with diabetes (PWD). The method may additionally include selecting a first profile of the first plurality of insulin delivery profiles based at least in part upon a comparison between the first plurality of future blood glucose values for each insulin delivery profile and at least one target blood glucose level. The method may also include delivering a first dose of insulin using an insulin pump for a second time interval after a previous dose of insulin that corresponds to a first action (or a series of first actions) in the first series of insulin delivery actions of the first profile. The second time interval may be shorter than the first time interval. The method may also include generating a second plurality of insulin delivery profiles for a time period extending from the end of the second time interval for a third time interval, and projecting a second plurality of future blood glucose values for each insulin delivery profile of the second plurality of insulin delivery profiles for a plurality of times spanning the third time interval. The method may also include delivering a second dose of insulin using the insulin pump for a fourth time interval after the end of the second time interval. The fourth time interval may be shorter than the third time interval.

In accordance with one or more methods of the present disclosure, the first series of insulin delivery actions may include delivering insulin at multiples, ratios, or a combination thereof of a baseline basal insulin rate.

In accordance with one or more methods of the present disclosure, the first series of insulin delivery actions may include delivering insulin at between 0x and 3x the baseline basal insulin rate (inclusive of endpoints).

In accordance with one or more methods of the present disclosure, the first plurality of insulin delivery profiles may include between 5 profiles and 100 profiles. In such cases, at least one profile may deliver insulin at 0x baseline basal rate for at least the second time interval, at least one profile may deliver insulin at the baseline basal rate for at least the second time interval, and at least one profile may deliver insulin at 2× baseline basal rate for at least the second time interval.

In accordance with one or more methods of the present disclosure, at least one of the first plurality of insulin delivery profiles may include an inflection point between a first insulin delivery amount for a first portion of the first series of insulin delivery actions and a second insulin delivery amount for a second portion of the first series of insulin delivery actions.

In accordance with one or more methods of the present disclosure, the first time interval may be at least 2 hours and no more than 6 hours and the second time interval may be at least 5 minutes and no more than 90 minutes.

In accordance with one or more methods of the present disclosure, the first time interval may be at least 2.5 hours and no more than 5.5 hours and the second time interval may be at least 7.5 minutes and no more than 60 minutes.

In accordance with one or more methods of the present disclosure, the first time interval may be least 3 hours and no more than 5 hours and the second time interval may be at least 10 minutes and no more than 30 minutes.

In accordance with one or more methods of the present disclosure, the first profile of the first plurality of insulin delivery profiles may be selected based on a calculated cost function for each of the first plurality of insulin delivery profiles.

In accordance with one or more methods of the present disclosure, the first profile may be selected based on having the lowest cost function. In such cases, differences between each projected future blood glucose level and one or more target blood glucose levels may increase a calculated cost function value for each insulin delivery profile.

In accordance with one or more methods of the present disclosure, the cost function value increase may be greater for differences where the projected blood glucose level is below the target blood glucose level compared to equal magnitude differences where the projected blood glucose level is above the target blood glucose level.

In accordance with one or more methods of the present disclosure, the cost function may include a bias or insulin delivery profiles that either maintain a delivery of insulin at a rate equal to the previously delivered rate, or that deliver insulin at a baseline basal rate.

In accordance with one or more methods of the present disclosure, predicting future blood glucose may include determining an effect on blood glucose due to carbohydrates, and determining an effect on blood glucose due to insulin.

In accordance with one or more methods of the present disclosure, the effect on blood glucose due to carbohydrates may be determined using the equation $$G_c = \frac{K_c(1-\alpha_c)B^{C_{dt}}}{(1-\alpha_c B)(1-B)}.$$

In accordance with one or more methods of the present disclosure, the effect on blood glucose due to insulin may be determined using the equation $$G_i = \frac{K_i(1-\alpha_c)B^{i_{dt}}}{(1-\alpha_i B)(1-B)}.$$

In accordance with one or more methods of the present disclosure, predicting future blood glucose may include determining the effect of insulin on board and carbohydrates on board.

In accordance with one or more methods of the present disclosure, the plurality of glucose sensor data points may be obtained from one of a continuous glucose monitor (CGM) or a blood glucose monitor (BGM).

In one or more embodiments, the present disclosure may include a system that includes a glucose configured to generate a plurality of glucose sensor data points, and a control device. The control device may be configured to generate a first plurality of insulin delivery profiles, and each of the first plurality of insulin delivery profiles may include a first series of insulin delivery actions spanning a first time interval. The control device may also be configured to project a first plurality of future blood glucose values for each insulin delivery profile of the first plurality of insulin delivery profiles for a plurality of times spanning the first time interval, and each of the projected future blood glucose values may be projected using at least one up-to-date blood glucose level from the glucose sensor. The control device may additionally be configured to select a first profile of the first plurality of insulin delivery profiles based at least in part upon a comparison between the first plurality of future blood glucose values for each insulin delivery profile and at least one target blood glucose level. The control device may also be configured to generate a signal to deliver a first dose of insulin for a second time interval after a previous dose of insulin. The first dose of insulin may correspond to a first action in the first series of insulin delivery actions of the first profile, and the second time interval may be shorter than the first time interval. The control device may additionally be configured to generate a second plurality of insulin delivery profiles for a time period extending from the end of the second time interval for a third time interval, and to project a second plurality of future blood glucose values for each insulin delivery profile of the second plurality of insulin delivery profiles for a plurality of times spanning the third time interval. The control device may also be configured to select a second profile of the second plurality of insulin delivery profiles based at least in part upon a comparison between the second plurality of future blood glucose values for each insulin delivery profile and at least one target blood glucose level. The control device may additionally be configured to generate a signal to deliver a second dose of insulin using the insulin pump for a fourth time interval after the end of the second time interval, the fourth time interval being shorter than the third time interval. The system may also include an insulin pump configured to deliver insulin based on the signal of the control device.

In accordance with one or more systems of the present disclosure, the control device may include a communication device to transmit the plurality of glucose sensor data points to a computing device.

In accordance with one or more systems of the present disclosure, the first plurality of insulin delivery profiles may include between 5 profiles and 100 profiles. In such cases, at least one profile may deliver insulin at 0x the baseline basal rate for at least the second time interval, at least one profile may deliver insulin at the baseline basal rate for at least the second time interval, and at least one profile may deliver insulin at 2x the baseline basal rate for at least the second time interval.

In accordance with one or more systems of the present disclosure, the first time interval may be at least 3 hours and no more than 5 hours and the second time interval may be at least 10 minutes and no more than 30 minutes.

In one or more embodiments, the present disclosure may include a method including delivering insulin, using an insulin pump and a controller, over a first diurnal time period based on a baseline basal insulin rate stored in memory. The controller may receive blood glucose data to control delivery of insulin via the insulin pump in amounts variable from the baseline basal insulin rate to control blood glucose levels for a person with diabetes (PWD). The method may also include modifying the baseline basal insulin rate stored in the memory for a second diurnal time period that is at least 20 hours after the first diurnal period based on an amount of insulin actually delivered during the first diurnal time period.

In accordance with one or more methods of the present disclosure, a carbohydrate-to-insulin ratio (CR) for the second diurnal time period may also be modified based on the amount of insulin actually delivered during the first diurnal time period.

In accordance with one or more methods of the present disclosure, an insulin sensitivity factor (ISF) for the second diurnal time period may also be modified based on the amount of insulin actually delivered during the first diurnal time period.

In accordance with one or more methods of the present disclosure, the second diurnal time period may include one of a same time period on another day or a time period within two hours prior to the same time period on another day.

In accordance with one or more methods of the present disclosure, the baseline basal insulin rate stored in memory for the second diurnal time period may be increased if a ratio of the amount of insulin actually delivered during the first diurnal time period to the amount dictated by the baseline basal insulin rate for the first diurnal time period exceeds a predetermined first threshold. Additionally, the baseline basal insulin rate stored in memory for the second diurnal time period may be decreased if the ratio falls below a predetermined second threshold.

In accordance with one or more methods of the present disclosure, the baseline basal insulin rate stored in memory for the second diurnal time period may be increased or decreased by a fixed amount or percentage that is less than the difference between the amount of insulin actually delivered during the first diurnal time period and the amount dictated by the baseline basal insulin rate.

In accordance with one or more methods of the present disclosure, the baseline basal rate stored in memory may be increased or decreased by a percentage between about 1% and about 5%.

In accordance with one or more methods of the present disclosure, a stored CR or a stored ISF for the second diurnal time period may also be increased or decreased by a fixed amount or percentage when the baseline basal rate is modified.

In accordance with one or more methods of the present disclosure, the baseline basal rate, CR, and ISF stored in memory may each be increased or decreased by a percentage between about 1% and about 5%. In some cases, each of CR, ISF, and BBR are each increased/decreased in lock step, with each of CR and ISF being increased by a percentage approximately equal to the percentage of a decrease to BBR for when there is a decrease in the BBR and each of CR and ISF being decreased by a percentage approximately equal to the percentage of an increase to BBR for when there is an increase in the BBR. In some cases, CR, ISF, and BBR can all be increased/decreased based on a predetermined relationship.

In accordance with one or more methods of the present disclosure, the baseline basal insulin rate stored in memory may be adjusted by an amount that is based on the ratio, but less than the difference between the amount of insulin actually delivered during the first diurnal time period and the amount dictated by the baseline basal insulin rate.

In accordance with one or more methods of the present disclosure, a stored CR and a stored ISF for the second diurnal time period may be increased when the basal rate is decreased and may be decreased when the basal rate is increased.

In accordance with one or more methods of the present disclosure, delivering insulin, using an insulin pump and controller, over a first diurnal time period may include generating a first plurality of insulin delivery profiles that each include a first series of insulin delivery actions spanning a first time interval and based on the baseline basal insulin rates stored in memory for a plurality of diurnal time periods within the first time interval. Delivering insulin may additionally include projecting a first plurality of future blood glucose values for each insulin delivery profile of the first plurality of insulin delivery profiles for a plurality of times spanning the first time interval, and each of the projected future blood glucose values may be projected using at least one up-to-date blood glucose level for the PWD. Delivering insulin may also include selecting a first profile of the first plurality of insulin delivery profiles based at least in part upon a comparison between the first plurality of future blood glucose values for each insulin delivery profile and at least one target blood glucose level. Delivering insulin may additionally include delivering a first dose of insulin for at least part of the first diurnal time period using the insulin pump for a second time interval, the second time interval being no greater than the first diurnal time period, and optionally repeating these steps until insulin is delivered for the entire first diurnal time period.

In accordance with one or more methods of the present disclosure, each action in the first series of insulin delivery actions may include one of delivering 0x, 1x, or 2x the baseline basal insulin rate.

In accordance with one or more methods of the present disclosure, the plurality of future blood glucose levels may be determined using an ISF, CR, or combination thereof stored in memory for the first diurnal time period.

In accordance with one or more methods of the present disclosure, the controller may receive insulin or food consumption data to control delivery of insulin.

In one or more embodiments, the present disclosure may include a system that includes an insulin pump configured to deliver insulin based on a message, a glucose sensor configured to generate blood glucose data, and a controller including memory. The controller may be configured to generate messages to deliver insulin over a first diurnal time period based on a baseline basal insulin rate stored in the memory. The controller may also be configured to receive blood glucose data from the glucose sensor to control generation of the messages to deliver insulin in amounts variable from the baseline basal insulin rate to control blood glucose levels for a person with diabetes (PWD). The controller may additionally be configured to modify the baseline basal insulin rate stored in the memory for a second diurnal time period that is at least 20 hours after the first diurnal period based on an amount of insulin actually delivered during the first diurnal time period.

In accordance with one or more systems of the present disclosure, the controller may be part of the insulin pump.

In accordance with one or more systems of the present disclosure, the controller may be a separate device from the insulin pump.

In one or more embodiments, the present disclosure may include a method that includes displaying to a user an interface at which the user inputs a fear of hypoglycemia index (FHI), the FHI corresponding to an acceptable probability of a blood glucose level being below a threshold blood glucose level. The method may also include receiving blood glucose data for a person with diabetes (PWD). The method may additionally include calculating a probability of the PWD having a blood glucose level below the threshold blood glucose level based on the variability of the received blood glucose data. The method may also include setting one or more target blood glucose levels to align the probability of the PWD having a blood glucose level below the threshold blood glucose level with the acceptable probability associated with the user input FHI. The method may additionally include delivering insulin, using the insulin delivery device, based on the target blood glucose level.

In accordance with one or more methods of the present disclosure, a plurality of target blood glucose levels may be set for a plurality of diurnal time periods and independently modified for each diurnal time period based on a calculated probability of the PWD having a blood glucose level falling below the threshold blood glucose level during that diurnal time period.

In accordance with one or more methods of the present disclosure, the insulin delivery device is an insulin pump.

In accordance with one or more methods of the present disclosure, delivering insulin, using the insulin pump, based on the one or more target blood glucose levels may include generating a first plurality of insulin delivery profiles, where each of the first plurality of basal insulin delivery profiles may include a first series of insulin delivery actions spanning a first time interval. Delivering insulin may also include selecting a first profile of the first plurality of basal insulin delivery profiles that approximates the one or more target blood glucose level based on projected blood glucose levels for each of the plurality of insulin delivery profiles. Delivering insulin may additionally include delivering a dose of insulin using the insulin pump for a second time interval after a previous dose of insulin, the dose of insulin corresponding to a first action in the first series of insulin delivery actions of the first profile, and the second time interval being shorter than the first time interval.

In accordance with one or more methods of the present disclosure, the first plurality of basal insulin delivery profiles may each be evaluated using a cost function that evaluates the differences between the projected blood glucose levels and the one or more target blood glucose levels, and the first profile may be selected based on the cost function.

In accordance with one or more methods of the present disclosure, the user interface may include an interactive feature with a plurality of possible FHI values by which the user inputs the FHI by selecting a displayed possible FHI.

In accordance with one or more methods of the present disclosure, the FHI options displayed include at least one of a numerical blood glucose level, a probability of going below a low threshold glucose level, a probability of going above a high threshold glucose level, and a textual description of a preferred glucose level, by which the user inputs the FHI.

In accordance with one or more methods of the present disclosure, the user may be the PWD, a caregiver to the PWD, or a healthcare professional.

In one or more embodiments, the present disclosure may include a system that includes an interactive display device configured to display an interface at which the user inputs a fear of hypoglycemia index (FHI). The FHI may correspond to an acceptable probability of crossing a threshold blood glucose level. The system may also include an insulin pump configured to deliver insulin based on a message, and a control device configured to calculate a probability of a person with diabetes (PWD) having a blood glucose level that falls below the threshold blood glucose level based on the variability of blood glucose levels for that PWD. The controller may also be configured to determine, based on the FHI and the probability of the PWD crossing the threshold blood glucose level, one or more target blood glucose levels to align the probability of the PWD having a blood glucose level that falls below the threshold blood glucose level with the acceptable probability associated with a user selected FHI. The controller may additionally be configured to determine an insulin delivery profile or rate based on the one or more target blood glucose levels, and generate the message to the insulin pump to deliver insulin based on the determined insulin delivery profile or rate.

In accordance with one or more systems of the present disclosure, the interactive display device and the control device may be components of the same device.

In accordance with one or more systems of the present disclosure, the interactive display device and the control device may be components of different devices.

In accordance with one or more systems of the present disclosure, the controller may store a plurality of target blood glucose levels for a plurality of diurnal time periods and may independently modify each diurnal time period based on a calculated probability of the PWD having a blood glucose level falling below the threshold blood glucose level during that diurnal time period.

In accordance with one or more systems of the present disclosure, the controller may determine an insulin delivery profile or rate by generating a first plurality of insulin delivery profiles, where each of the first plurality of basal insulin delivery profiles may include a first series of insulin delivery actions spanning a first time interval. The controller may also determine an insulin delivery profile or rate by selecting a first profile of the first plurality of basal insulin delivery profiles that approximates the one or more target blood glucose levels based on projected blood glucose levels for each of the plurality of insulin delivery profiles. In such a case, generating the message may be further based on a dose of insulin corresponding to a first action in the first series of insulin delivery actions of the first profile, and the second time interval may be shorter than the first time interval.

In accordance with one or more systems of the present disclosure, the first plurality of basal insulin delivery profiles may each be evaluated using a cost function evaluating the differences between the projected blood glucose levels and at least the one or more target blood glucose levels, and the first profile may be selected based on the cost function.

In accordance with one or more systems of the present disclosure, the user interface may include an interactive feature with a plurality of possible FHI values by which the user inputs the FHI.

In accordance with one or more systems of the present disclosure, the FHI options displayed may include at least one of a numerical blood glucose level, a probability of going below a low threshold glucose level, a probability of going above a high threshold glucose level, and a textual description of a preferred glucose level, by which the user inputs the FHI.

In one or more embodiments, the present disclosure may include a non-transitory computer readable medium containing instructions that, when executed by a processor, are configured to perform operations. The operations may include receiving a selection of a fear of hypoglycemia index (FHI), where the FHI may correspond to an acceptable probability of crossing a threshold blood glucose level. The operations may also include calculating a probability of a person with diabetes (PWD) having a blood glucose level falling below the threshold blood glucose level based on variability of blood glucose values for the PWD. The operations may additionally include setting, based on the FHI and the probability of the PWD having a blood glucose level falling below the threshold blood glucose level, one or more target blood glucose levels to align the probability of the PWD having a blood glucose level falling below the threshold blood glucose level with the acceptable probability associated with a user selected FHI. The operations may additionally include generating a message to an insulin pump to deliver insulin based on the one or more target blood glucose levels.

In one or more embodiments, the present disclosure may include a method that includes receiving up-to-date blood glucose data for a person with diabetes (PWD), and determining basal insulin dosages for the PWD based at least in part on one or more baseline basal rates stored in memory on a controller, with the received up-to-date blood glucose data and at least one target blood glucose level stored in the memory. The method may also include delivering one or more of the determined basal insulin dosages to the PWD, and modifying the one or more target blood glucose levels stored in the memory based on a variability of blood glucose data for the PWD. The method may also include receiving an input at an electronic device of a temporary override indicating a user preference to reduce the likelihood that the PWD has a hypoglycemic event or a user preference to reduce the likelihood that the PWD has a hyperglycemic event. The method may also include determining one or more temporary target blood glucose levels based on the received user input, where the temporary target blood glucose levels may be greater than the modified one or more target blood glucose levels if the user preference is to reduce the likelihood that the PWD has a hypoglycemic event. Alternatively, the temporary target blood glucose levels may be lower than the modified one or more target blood glucose levels if the user preference is to reduce the likelihood that the PWD has a hyperglycemic event. The method may additionally include delivering one or more doses of basal insulin for the temporary period of time based on the one or more temporary target blood glucose levels.

In accordance with one or more methods of the present disclosure, the basal insulin dosages for the PWD may be determined by generating a first plurality of insulin delivery profiles, where each of the first plurality of insulin delivery profiles may include a first series of insulin delivery actions based on the one or more stored baseline basal insulin rates spanning a first time interval. The basal insulin dosages may also be determined by projecting a first plurality of future blood glucose values for each insulin delivery profile of the first plurality of insulin delivery profiles for a plurality of times spanning the first time interval, where each projected future blood glucose values may be projected using at least one of the received up-to-date blood glucose levels for the PWD. The basal insulin dosages may additionally be determined by selecting a first profile of the first plurality of insulin delivery profiles based at least in part upon a comparison between the first plurality of future blood glucose values for each insulin delivery profile and the one or more target blood glucose levels.

In accordance with one or more methods of the present disclosure, the first time interval may be longer than the time interval for which the selected first profile is used to deliver insulin prior to the determination of a next dose of insulin using the same process.

In accordance with one or more methods of the present disclosure, the process of generating a plurality of insulin delivery profiles may be used during the temporary period of time, and the selected profile may be based on the one or more temporary target blood glucose levels during the temporary period of time.

In accordance with one or more methods of the present disclosure, receiving an input may include receiving a selection of one of a numerical target blood glucose level, a selection of an activity, or a selection of a textual description of a preferred blood glucose level.

In accordance with one or more methods of the present disclosure, the one or more temporary target blood glucose levels may be set at a fixed percentage increase or decrease from the one or more modified target blood glucose levels, and may be optionally limited by a prestored or particular maximum or minimum value for target blood glucose levels.

In accordance with one or more methods of the present disclosure, the one or more temporary target blood glucose levels may be set at a fixed numerical increase or decrease from the one or more modified target blood glucose levels, and may be optionally limited by a prestored or particular maximum or minimum value for target blood glucose levels.

In accordance with one or more methods of the present disclosure, all target blood glucose levels are limited to values between 100 mg/dL and 160 mg/dL.

In accordance with one or more methods of the present disclosure, receiving an input may include receiving a length of time for the temporary period of time.

In accordance with one or more methods of the present disclosure, the memory may store a baseline basal rate and a target blood glucose level for a plurality of diurnal time periods.

In accordance with one or more methods of the present disclosure, the one or more target blood glucose levels may be modified based on a determination of a probability of the PWD having a blood glucose level below a threshold blood glucose level based on the variability of received blood glucose data over multiple days. In such cases, the one or more target blood glucose levels may be modified to align the probability of the PWD having a blood glucose level below the threshold blood glucose level with an acceptable probability of the PWD having a blood glucose level falling below the threshold blood glucose level.

In one or more embodiments, the present disclosure may include a system that includes an insulin pump configured to deliver insulin based on a message, a glucose sensor configured to generate a plurality of glucose sensor data points, an interface for receiving a user preference to reduce the likelihood that a person with diabetes (PWD) has a hypoglycemic event or a user preference to reduce the likelihood that the PWD has a hyperglycemic event, and a controller. The controller, the user interface, or a combination thereof, may be configured to receive up-to-date blood glucose data from the glucose sensor, and determine basal insulin dosages based at least in part on one or more baseline basal rates stored in memory on the controller, where the received up-to-date blood glucose data, and at least one target blood glucose level may be stored in the memory. The controller, the user interface, or a combination thereof, may additionally be configured to generate the message to the insulin pump to deliver the determined basal insulin dosages, modify the one or more target blood glucose levels stored in the memory based on a variability of blood glucose data from the glucose sensor, and receive the user preference. The controller, the user interface, or a combination thereof, may also be configured to determine one or more temporary target blood glucose levels based on the received user preference, where the temporary target blood glucose levels may be greater than the modified one or more target blood glucose levels if the user preference is to reduce the likelihood that the PWD has a hypoglycemic event. Alternatively, the temporary target blood glucose levels may be lower than the modified one or more target blood glucose levels if the user preference is to reduce the likelihood that the PWD has a hyperglycemic event. The controller, the user interface, or a combination thereof, may also be configured to generate the message to the insulin pump to deliver doses of basal insulin for the temporary period of time based on the one or more temporary target blood glucose levels.

In accordance with one or more systems of the present disclosure, the controller may be part of the insulin pump.

In accordance with one or more systems of the present disclosure, the controller may be a separate device from the insulin pump.

The details of one or more implementations of various embodiments are set forth in the accompanying drawings and the description below. Other features, objects, and advantages of the various embodiments will be apparent from the description and drawings, and from the claims.

It is to be understood that both the foregoing general description and the following detailed description are merely examples and explanatory and are not restrictive of the claims.

BRIEF DESCRIPTION OF THE DRAWINGS

Example embodiments will be described and explained with additional specificity and detail through the use of the accompanying drawings in which.

DESCRIPTION OF EMBODIMENTS

Figure 1:
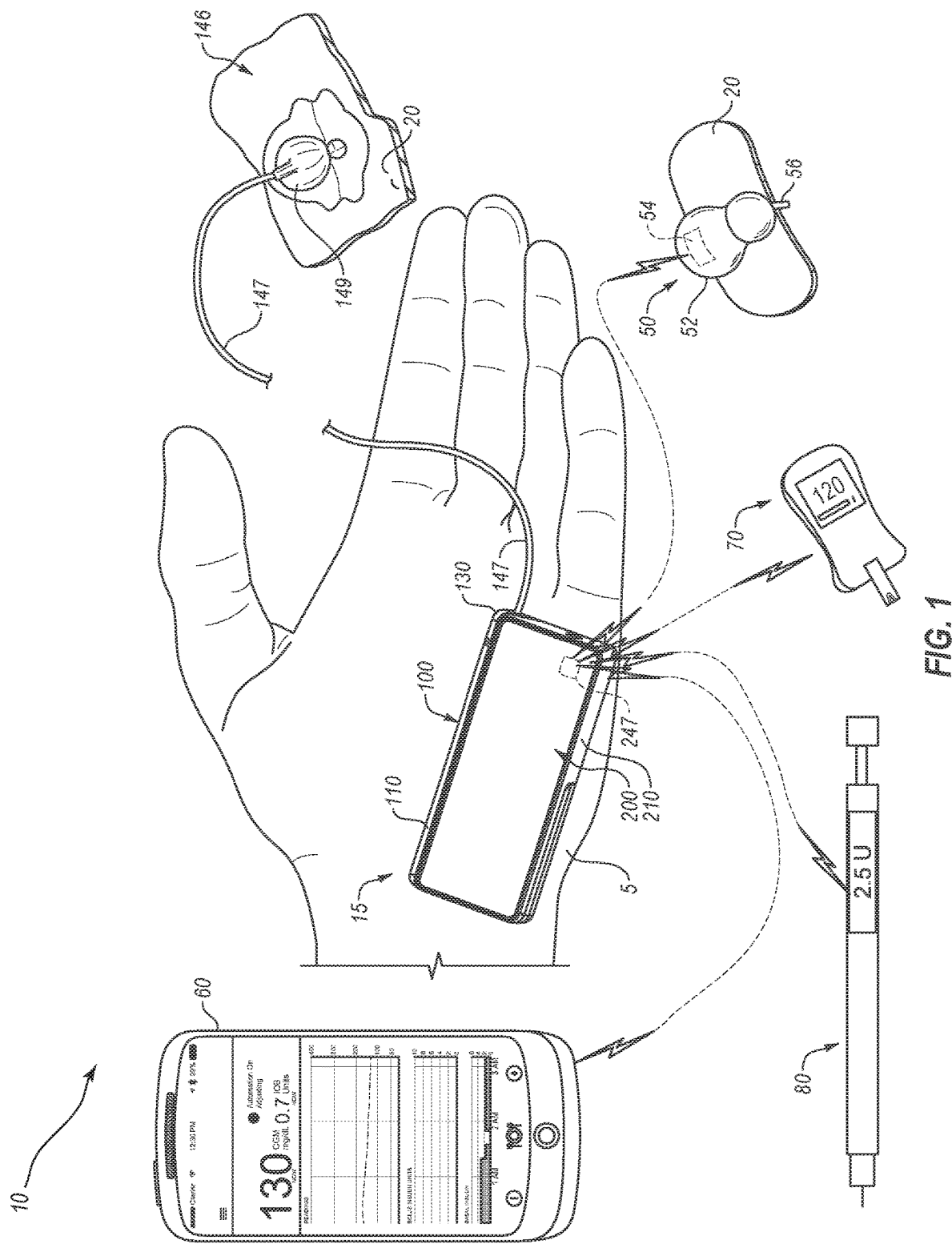
FIG. 1 provides an example diabetes management system (DMS)

Medicine delivery systems and methods provided herein may be used and performed, respectively, by a user, for example, a person with diabetes (PWD). The PWD may live with type 1, type 2, or gestational diabetes. In some cases, a user can be a healthcare professional or caregiver for a PWD.

Methods and systems provided herein can use information from a glucose measurement device (e.g., a continuous glucose monitor) to have up-to-date blood glucose data (e.g., a plurality of blood glucose data points each hour) for the PWD in order to determine how to adjust basal insulin delivery rates. In some cases, methods and systems provided herein can use blood glucose data from both one or more continuous glucose monitors and one or more blood glucose meters. Methods and systems provided herein can be part of a hybrid closed-loop system (for example, where basal rates can be adjusted automatically and the PWD can manually enter or deliver a bolus). In some cases, methods and system provided herein can be part of a fully closed-loop system (for example, where basal rates can be adjusted automatically and boluses can be delivered automatically). In some cases, "up-to-date" may mean less than 1 hour old, less than 30 minutes old, or less than 15 minutes old.

Methods and systems provided herein can use a model to predict multiple future blood glucose levels for multiple different basal insulin delivery profiles or basal insulin delivery rates, and select one of the basal insulin delivery profiles or basal insulin delivery rates based on prediction of which profile or rate will approximate a target blood glucose level, or more specifically, select the profile that minimizes the differences between the predicted future blood glucose values and one or more target blood glucose values. In some cases, the profile that minimizes, lessons, or lowers variations from one or more target blood glucose levels in the future may be selected. The selected basal profile can then be delivered to the PWD at least until a process of evaluating different basal insulin delivery profiles or rates is repeated. In some cases, methods and systems provided herein can repeat a process of evaluating multiple different basal insulin delivery profiles or basal insulin delivery rates at a time interval that is less than the time interval for the plurality of future predicted blood glucose values. For example, in some cases, the time interval between evaluating and selecting from multiple different basal insulin delivery profiles or basal insulin delivery rates can be less than one hour while the plurality of future predicted blood glucose values can extend over a time interval of at least two hours into the future. In some cases of methods and systems provided herein, each of the evaluated basal insulin delivery profiles or rates can extend for a time interval greater than the time interval between evaluation processes. In some cases, methods and systems provided herein can evaluate insulin delivery profiles and rates that extend at least two hours into the future and predicted blood glucose values can also be predicted over a time interval that extends at least two hours into the future. In some cases, the profiles/rates and time interval of predicted future blood glucose values extends at least three hours into the future. In some cases, the profiles/rates and time interval of predicted future blood glucose values extends a period of time (e.g., at least four hours) into the future. In some cases, the profiles/rates and time interval of predicted future blood glucose values extends at least five hours into the future. As used herein, the term blood glucose level may include any measurement that estimates or correlates with blood glucose level, such as a detection of glucose levels in interstitial fluids, urine, or other bodily fluids or tissues.

The different basal insulin delivery profiles or rates for each evaluation process can be generated using any suitable techniques. In some cases, multiple profiles or delivery rates are generated using one or more user-specific dosage parameters. In some cases, one or more user-specific dosage parameters can be entered by a user, calculated by information entered by a user, and/or calculated by monitoring data generated from the PWD (e.g., monitoring insulin delivery rates and blood glucose data while the PWD is using a pump in an open loop mode). In some cases, methods and systems provided herein can modify user-specific dosage parameters over time based on one or more selected basal insulin delivery profiles or rates and/or other data obtained from the PWD. In some cases, the user-specific dosage parameters can be dosage parameters that are commonly used in the treatment of diabetes, such as average total daily insulin, total daily basal (TDB) insulin, average basal rate, insulin sensitivity factor (ISF), and carbohydrate-to-insulin ratio (CR). For example, in some cases, a PWD's average basal rate can be used to calculate multiple different basal insulin delivery profiles based on multiples or fractions of the average basal rate used over different intervals of time. In some cases, methods and systems provided herein can use time-interval-specific user-specific dosage parameters (e.g., a time-interval-specific baseline basal rate). In some cases, methods and systems provided herein can make adjustments to time-interval-specific user-specific dosage parameters for each time interval for where a delivered basal rate varies from a baseline basal rate for that time interval. In some cases, user-specific dosage parameters are specific for time intervals of two hours or less, one hour or less, thirty minutes or less, or fifteen minutes or less. For example, in some cases, methods and systems provided herein can store a baseline basal rate for the hour between 1 PM and 2 PM, and can adjust the baseline basal rate for that hour up if the method or system delivers more basal insulin during that time period and adjust the baseline basal rate down if the method or system delivers less basal insulin during that time period. In some cases, adjustments to user-specific dosage parameters can be based on a threshold variation and/or can be limited to prevent excessive adjustments to user-specific dosage parameters. For example, in some cases, a daily adjustment to a user-specific dosage parameter can be limited to less than 10%, less than 5%, less than 3%, less than 2%, or to about 1%. In some cases, an adjustment to a baseline basal rate is less than a difference between the amount of basal insulin actually delivered and the baseline basal for a specific period of time (e.g., if a baseline basal rate is 1 U/hour and systems or methods provided herein actually delivered 2 U for the previous hour, the adjustment to any baseline basal rate based on that difference would be less than 1 U/hour).

Methods and systems provided herein can use any appropriate model to predict multiple future blood glucose values. In some cases, predictive models can use one or more current or recent blood glucose measurements (e.g., from blood glucose meter and/or a continuous glucose monitor), estimates of rates of change of blood glucose levels, an estimation of unacted carbohydrates, and/or an estimation of unacted insulin. In some cases, predictive models can use one or more user-specific dosage parameters in predicting multiple blood glucose values over a future time interval for multiple different basal insulin delivery profiles or rates over that same future time interval. As discussed above, that future time interval can be at least two hours, at least three hours, or at least four hours, at least five hours, etc. User-specific dosage parameters, which can be time-interval-specific, can also be used in determining an estimation of unacted carbohydrates and/or an estimation of unacted insulin. In some cases, an estimation of unacted carbohydrates and/or an estimation of unacted insulin can use a simple decay function. In some cases, an estimate of unacted insulin can be determined using an Insulin On Board (IOB) calculation, which are common in the art of treating diabetes. In some cases, an IOB calculation used in a predictive model used in methods and systems provided herein can consider insulin delivered to the PWD during the delivery of a bolus. In some cases, the IOB calculation can additionally add or subtract to the IOB based on changes to the basal insulin delivery rate from a baseline basal rate. In some cases, an estimate of unacted carbohydrates can be determined using a Carbohydrates On Board (COB) calculation, which can be based on a decay function and announced meals. In some cases, predictive models used in methods and systems provided herein can also consider the non-carbohydrate components of a meal. In some cases, methods and systems provided herein can infer an amount of carbohydrates from an unannounced meal due to a spike in up-to-date blood glucose data. In some cases, predictive models used in methods and systems provided herein can additionally consider additional health data or inputs, which may indicate that the PWD is sick, exercising, experiencing menses, or some other condition that may alter the PWD's reaction to insulin and/or carbohydrates. In some cases, at least an IOB, a COB, an insulin sensitivity factor (ISF), and a carbohydrate-to-insulin ratio (CR) are used to predict future blood glucose values for each evaluated basal insulin delivery profile or rate.

Methods and systems provided herein can set one or more blood glucose targets using any suitable technique. In some cases, a blood glucose target can be fixed, either by a user or preprogrammed into the system. In some cases, the target blood glucose level can be time interval specific (e.g., based on diurnal time segments). In some cases, a user can temporarily or permanently adjust the target blood glucose level. In some cases, methods and systems provided herein can analyze the variability of blood glucose data for specific days of the week and/or based on other physiological patterns and adjust the blood glucose targets for that individual based on the specific day of the week or based on other physiological patterns. For example, a PWD may have certain days of the week when they exercise and/or PWD may have different insulin needs based on a menses cycle.

Methods and systems provided herein can evaluate each basal insulin delivery profile or rate to select the profile or rate that minimizes a variation from the one or more blood glucose targets using any appropriate method. In some cases, methods and systems provided herein can use a cost function to evaluate differences between the predicted blood glucose values for each basal insulin delivery profile or rate and blood glucose targets, potentially specified for a diurnal time segment. Methods and systems provided herein can then select a basal profile or rate that produces the lowest cost function value. Methods and systems provided herein can use any suitable cost function. In some cases, cost functions can sum the absolute value of the difference between each predicted blood glucose value and each blood glucose target. In some cases, cost functions used in methods and systems provided herein can use square of the difference. In some cases, cost functions used in methods and systems provided herein can assign a higher cost to blood glucose values below the blood glucose target in order reduce the risk of a hypoglycemic event. In some cases, the cost function can include a summation of the absolute values of a plurality of predicted deviations, squared deviations, log squared deviations, or a combination thereof. In some cases, a cost function can include variables unrelated to the predicted blood glucose values. For example, a cost function can include a penalty for profiles that do not deliver 100% of the BBR, thus adding a slight preference to use 100% of BBR. In some cases, methods and systems provided herein can include a cost function that provides a slight preference to keep the existing basal modification for every other interval (e.g., a second 15 minute segment), which could reduce the variability in basal insulin delivery rates in typical situations, but allow for more critical adjustments.

Methods and systems provided herein can receive various inputs from a user related to the delivery of basal insulin. In some cases, a user may input a fear of hypoglycemia (FHI) index. The FHI may indicate the preference for or reticence to experience certain blood glucose levels by the PWD. For example, the FHI may indicate that the PWD prefers "high" blood glucose levels (e.g., blood glucose levels above a threshold); or as another example, the FHI may indicate that the PWD is concerned about "going low" (e.g., blood glucose levels below a threshold). In some cases, the FHI may correspond to a threshold and an acceptable probability of crossing the threshold, including using the threshold to signify going high or using the threshold to signify going low, or both. In some cases, a probability of the PWD crossing the threshold may be determined and a baseline basal insulin rate may be modified to more closely align the acceptable probability of crossing the threshold with the actual probability of crossing the threshold. Additionally or alternatively, the FHI may be used in other ways in methods and systems of the present disclosure. For example, modification of the baseline basal insulin rate for a diurnal period may be modified one way for a high FHI and another way for a low FHI. As another example, multiple profiles of insulin delivery steps may use one set of possible steps for a high FHI, and another set of possible steps for a low FHI.

Methods and systems provided herein can modify or alter an insulin delivery profile or rate in any number of ways. In some cases, a user may select a temporary override to indicate a user preference for a particular blood glucose level. For example, the PWD may indicate that they are going for a long drive and do not want to have their blood glucose levels drop below a certain level, and so may designate a target blood glucose level higher than their normal target blood glucose level, which may be set for a particular or indefinite length of time. In some cases, methods and systems provided herein may modify or otherwise select a new profile or rate from multiple profiles that corresponds to the blood glucose level from the temporary override. In some cases, methods and systems provided herein can permit a user to merely indicate a reduced tolerance for the risk of going low and can determine a temporary blood glucose level based on the variability of blood glucose data for that PWD for previous days (optionally for a particular diurnal time segment).

Methods and systems provided herein can store a plurality of user-specific dosage parameters (e.g., BBR, CR, and ISF) as different values for a plurality of different diurnal time segments. As used herein, "diurnal time segments" periods of time during each day, such that the methods and systems will repeat use of each diurnal-specific user-specific dosage parameter during the same time on subsequent days if a stored diurnal-specific user-specific dosage parameter is not modified or change, thus the use of the stored diurnal-specific user-specific dosage parameter will wrap each day. Methods and systems provided herein, however, can be adapted to make daily (or more or less frequent) adjustments to each diurnal-specific user-specific dosage parameter based on the operation of the system. Methods and systems provided herein may additionally store settings or adjustments for specific days of the week or for other repeating cycles.

After a basal insulin delivery profile or rate is selected, methods and systems provided herein can include the delivery of basal insulin to the PWD according to the selected basal insulin profile or rate for any suitable period of time. In some cases, methods and systems provided herein may supply basal insulin according to the selected basal insulin delivery profile or rate for a predetermined amount of time that may be less than the time interval of the evaluated basal insulin delivery profiles or rates. For example, methods and systems provided herein may analyze projected blood glucose values for basal insulin delivery profiles or rates that last over the next four hours but repeat the process of selecting a new basal insulin delivery profile or rate every fifteen minutes. In some cases, methods and systems provided herein can delay or suspend basal insulin delivery during the delivery of a bolus, which can be triggered by a user requesting a bolus.

As used herein, "basal insulin delivery" has its normal and customary meaning within the art of the treatment of diabetes. Although basal rates are expressed as a continuous supply of insulin over time, basal insulin delivery may constitute multiple discrete deliveries of insulin at regular or irregular intervals. In some cases, methods and systems provided herein may only be able to deliver insulin in discrete fractions of a unit. For example, some insulin delivery devices can only deliver insulin in a dose that are an integer multiple of 0.05 unit or 0.1 unit. In some cases, a delivery of basal insulin can include a delivery of insulin at predetermined time intervals less than or equal to fifteen minutes apart or less, ten minutes apart or less, or five minutes apart or less. In some cases, the time interval between discrete basal insulin deliveries can be determined based on the basal insulin delivery rate (e.g., a basal rate of 1.0 unit/hour might result in the delivery of 0.1 unit every six minutes). As used herein, the term "bolus" has its normal and customary meaning with the art of the treatment of diabetes, and can refer to a bolus delivered in order to counteract a meal (i.e., a meal-time bolus) and/or to correct for elevated blood glucose levels (i.e., a correction bolus).

Methods and systems provided herein can in some cases include multiple delivery modes. In some cases, methods and systems provided herein can monitor the presence of blood glucose using one or more blood glucose measuring devices or methods, control or monitor the dispensation of medicine, and determine and/or update the user-specific dosage parameters regardless of the operating mode. For example, possible operating modes could include closed-loop or hybrid closed-loop modes that automatically adjust basal rates based on continuous glucose monitoring data (CGM) and other user-specific dosage parameters (e.g., baseline basal rate (BBR), insulin sensitivity factor (ISF), and carbohydrate-to-insulin ratio (CR)), modes that can use blood glucose monitor (BGM) data to update user-specific dosage parameters (e.g., BBRs, ISFs, and CRs) for different time blocks over longer periods of time, manual modes that require a patient to manually control the therapy program using an insulin pump, and advisory modes that recommend dosages for a PWD to inject using an insulin pen or syringe. By determining optimized control parameters that work across delivery modes, systems and methods provided herein can provide superior analyte control even when a PWD switches to a different delivery mode. For example, methods and systems provided herein may be forced to switch away from a hybrid closed-loop delivery mode that adjusts basal insulin delivery away from a BBR if a continuous glucose monitor malfunctions or the system otherwise loses access to continuous data. In some cases, data can be collected when the system is in an advisory or manual mode to optimize control parameters in preparation for a PWD to switch to a hybrid closed-loop system (e.g., in preparation for a PWD to start use of a continuous glucose monitor (CGM) and/or an insulin pump).

Methods and systems provided herein can include an insulin pump and at least one blood glucose measurement device in communication with the insulin pump. In some cases, the blood glucose measurement device can be a CGM adapted to provide blood glucose measurements at least every fifteen minutes. In some cases, methods and systems provided herein include a CGM adapted to provide blood glucose measurements at least every ten minutes. In some cases, methods and systems provided herein include a CGM adapted to provide blood glucose measurements every five minutes. Methods and systems provided herein additionally include a controller adapted to determine an amount of basal insulin for delivery to a PWD and memory to store multiple user-specific dosage parameters. In some cases, the controller can be part of an insulin pump. In some cases, a controller can be part of a remote device, which can communicate wirelessly with an insulin pump. In some cases, the controller can communicate wirelessly with a CGM. In some cases, methods and systems provided herein can additionally include a user interface for displaying data and/or receiving user commands, which can be included on any component of a system provided herein. In some cases, the user interface can be part of a smartphone. In some cases, a user can input information on the user interface to trigger methods and systems provided herein to deliver a bolus of insulin. In some cases, methods and systems provided herein can use a blood glucose meter adapted to use test strip as a blood glucose measurement device. In some cases, methods and systems provided herein can additionally include an insulin pen, which can optionally communicate wirelessly with a controller.

Example Diabetes Management System

FIG. 1 depicts an example diabetes management system 10 including a pump assembly 15 for insulin and a continuous glucose monitor (CGM) 50. As shown, the continuous glucose monitor 50 is in wireless communication with pump assembly 15. In some cases, a continuous glucose monitor can be in wired communication with pump assembly 15. In some cases, not shown, a continuous glucose monitor can be incorporated into an insulin pump assembly. As shown, pump assembly 15 can include a reusable pump controller 200 that forms part of the pump assembly 15. In some cases, reusable pump controller 200 is adapted to determine one or more basal delivery rates. In some cases, continuous glucose monitor 50 can act as a controller adapted to communicate basal delivery rates to pump assembly 15.

Pump assembly 15, as shown, can include reusable pump controller 200 and a disposable pump 100, which can contain a reservoir for retaining insulin. A drive system for pushing insulin out of the reservoir can be included in either the disposable pump 100 or the reusable pump controller 200 in a controller housing 210. Reusable pump controller 200 can include a wireless communication device 247, which can be adapted to communicate with a wireless communication device 54 of continuous glucose monitor 50 and other diabetes devices in the system, such as those discussed below. In some cases, pump assembly 15 can be sized to fit within a palm of a hand 5. Pump assembly 15 can include an infusion set 146. Infusion set 146 can include a flexible tube 147 that extends from the disposable pump 100 to a subcutaneous cannula 149 that may be retained by a skin adhesive patch (not shown) that secures the subcutaneous cannula 149 to the infusion site. The skin adhesive patch can retain the cannula 149 in fluid communication with the tissue or vasculature of the PWD so that the medicine dispensed through tube 147 passes through the cannula 149 and into the PWD's body. A cap device 130 can provide fluid communication between an output end of an insulin cartridge (not shown) and tube 147 of infusion set 146. Although pump assembly 15 is depicted as a two-part insulin pump, one piece insulin pumps are also contemplated. Additionally, insulin pump assemblies used in methods and systems provided herein can alternatively be a patch pump.

Continuous glucose monitor 50 (e.g., a glucose sensor) can include a housing 52, a wireless communication device 54, and a sensor shaft 56. The wireless communication device 54 can be contained within the housing 52 and the sensor shaft 56 can extend outward from the housing 52. In use, the sensor shaft 56 can penetrate the skin 20 of a user to make measurements indicative of the PWD's blood glucose level or the like. In some cases, the sensor shaft 56 can measure glucose or another analyte in interstitial fluid or in another fluid and correlate that to blood glucose levels. In response to the measurements made by the sensor shaft 56, the continuous glucose monitor 50 can employ the wireless communication device 54 to transmit data to a corresponding wireless communication device 247 housed in the pump assembly 15. In some cases, the continuous glucose monitor 50 may include a circuit that permits sensor signals (e.g., data from the sensor shaft 56) to be communicated to the wireless communication device 54. The wireless communication device 54 can transfer the collected data to reusable pump controller 200 (e.g., by wireless communication to the wireless communication device 247). Additionally or alternatively, the system 10 may include another glucose monitoring device that may utilize any of a variety of methods of obtaining information indicative of a PWD's blood glucose levels and transferring that information to reusable pump controller 200. For example, an alternative monitoring device may employ a micropore system in which a laser porator creates tiny holes in the uppermost layer of a PWD's skin, through which interstitial glucose is measured using a patch. In the alternative, the monitoring device can use iontophoretic methods to non-invasively extract interstitial glucose for measurement. In other examples, the monitoring device can include non-invasive detection systems that employ near IR, ultrasound or spectroscopy, and particular implementations of glucose-sensing contact lenses. In other examples, the monitoring device can include detect glucose levels using equilibrium fluorescence detectors (e.g., sensors including a diboronic acid receptor attached to a fluorophore). Furthermore, it should be understood that in some alternative implementations, continuous glucose monitor 50 can be in communication with reusable pump controller 200 or another computing device via a wired connection. In some cases, continuous glucose monitor 50 can be adapted to provide blood glucose measurements for a PWD when in use for the PWD at regular or irregular time intervals. In some cases, continuous glucose monitor 50 can detect blood glucose measurements at least every thirty minutes, at least every fifteen minutes, at least every ten minutes, at least every five minutes, or about every minute. In some cases, continuous glucose monitor 50 can itself determine a basal delivery rate using methods provided herein and communicate that basal rate to the pump assembly 15. In some cases, continuous glucose monitor 50 can transmit blood glucose measurement data to reusable pump controller 200 and reusable pump controller 200 can use methods provided herein to determine a basal delivery rate. In some cases, a remote controller can receive glucose data from continuous glucose monitor 50, determine a basal delivery rate using methods provided herein, and communicate the basal rate to pump assembly 15.

Diabetes management system 10 may optionally include a blood glucose meter (BGM) 70 (e.g., a glucose sensor). In some cases, blood glucose meter 70 can be in wireless communication with reusable pump controller 200. Blood glucose meter 70 can take a blood glucose measurement using one or more test strips (e.g., blood test strips). A test strip can be inserted into a strip reader portion of the blood glucose meter 70 and then receive the PWD's blood to determine a blood glucose level for the PWD. In some cases, the blood glucose meter 70 is configured to analyze the characteristics of the PWD's blood and communicate (e.g., via a BLUETOOTH® wireless communication connection) the information to reusable pump controller 200. In some cases, a user can manually input a glucose meter reading. The blood glucose meter 70 can be manually operated by a user and may include an output subsystem (e.g., display, speaker) that can provide the user with blood glucose readings that can be subsequently entered into the controller or user interface to collect the data from an unconnected BGM into the system. The blood glucose meter 70 may be configured to communicate data (e.g., blood glucose readings) obtained to reusable pump controller 200 and/or other devices, such as a mobile computing device 60 (e.g., a control device). Such communication can be over a wired and/or wireless connection, and the data can be used by system 10 for a number of functions (e.g., calibrating the continuous glucose monitor 50, confirming a reading from the continuous glucose monitor 50, determining a more accurate blood glucose reading for a bolus calculation, detecting a blood glucose level when the continuous glucose monitor 50 is malfunctioning).

In some cases, the system 10 can further include a mobile computing device 60 that can communicate with the reusable pump controller 200 through a wireless and/or wired connection with the reusable pump controller 200 (e.g., via a BLUETOOTH® wireless communication connection or a near-field communication connection). In some cases, the mobile computing device 60 communicates wirelessly with other diabetes devices of system 10. The mobile computing device 60 can be any of a variety of appropriate computing devices, such as a smartphone, a tablet computing device, a wearable computing device, a smartwatch, a fitness tracker, a laptop computer, a desktop computer, and/or other appropriate computing devices. In some cases (for example, where the reusable pump controller 200 does not determine a basal delivery rate), the mobile computing device 60 can receive and log data from other elements of the system 10 and determine basal delivery rates using methods provided herein. In some cases, a user can input relevant data into the mobile computing device 60. In some cases, the mobile computing device 60 can be used to transfer data from the reusable pump controller 200 to another computing device (e.g., a back-end server or cloud-based device). In some cases, one or more methods provided herein can be performed or partially performed by the other computing device. In some cases, the mobile computing device 60 provides a user interface (e.g., graphical user interface (GUI), speech-based user interface, motion-controlled user interface) through which users can provide information to control operation of the reusable pump controller 200 and the system 10. For example, the mobile computing device 60 can be a mobile computing device running a mobile app that communicates with reusable pump controller 200 over short-range wireless connections (e.g., BLUETOOTH® connection, Wi-Fi Direct connection, near-field communication connection, etc.) to provide status information for the system 10 and allow a user to control operation of the system 10 (e.g., toggle between delivery modes, adjust settings, log food intake, change a fear of hypoglycemia index (FHI), confirm/modify/cancel bolus dosages, and the like).

Optionally, system 10 may include a bolus administering device 80 (e.g., a syringe, an insulin pen, a smart syringe with device communication capabilities, or the like) through which bolus dosages can be manually administered to a PWD. In some cases, a suggested dosage for a bolus to be administered using the bolus administering device 80 can be output to a user via the user interface of reusable pump controller 200 and/or the user interface of the mobile computing device 60. In some cases, the bolus administering device 80 can communicate through a wired and/or wireless connection with reusable pump controller 200 and/or the mobile computing device 60. In some cases, system 10 can allow users to input insulin deliveries made using a syringe or insulin pen.

Operation of a Diabetes Management System

Figure 2:
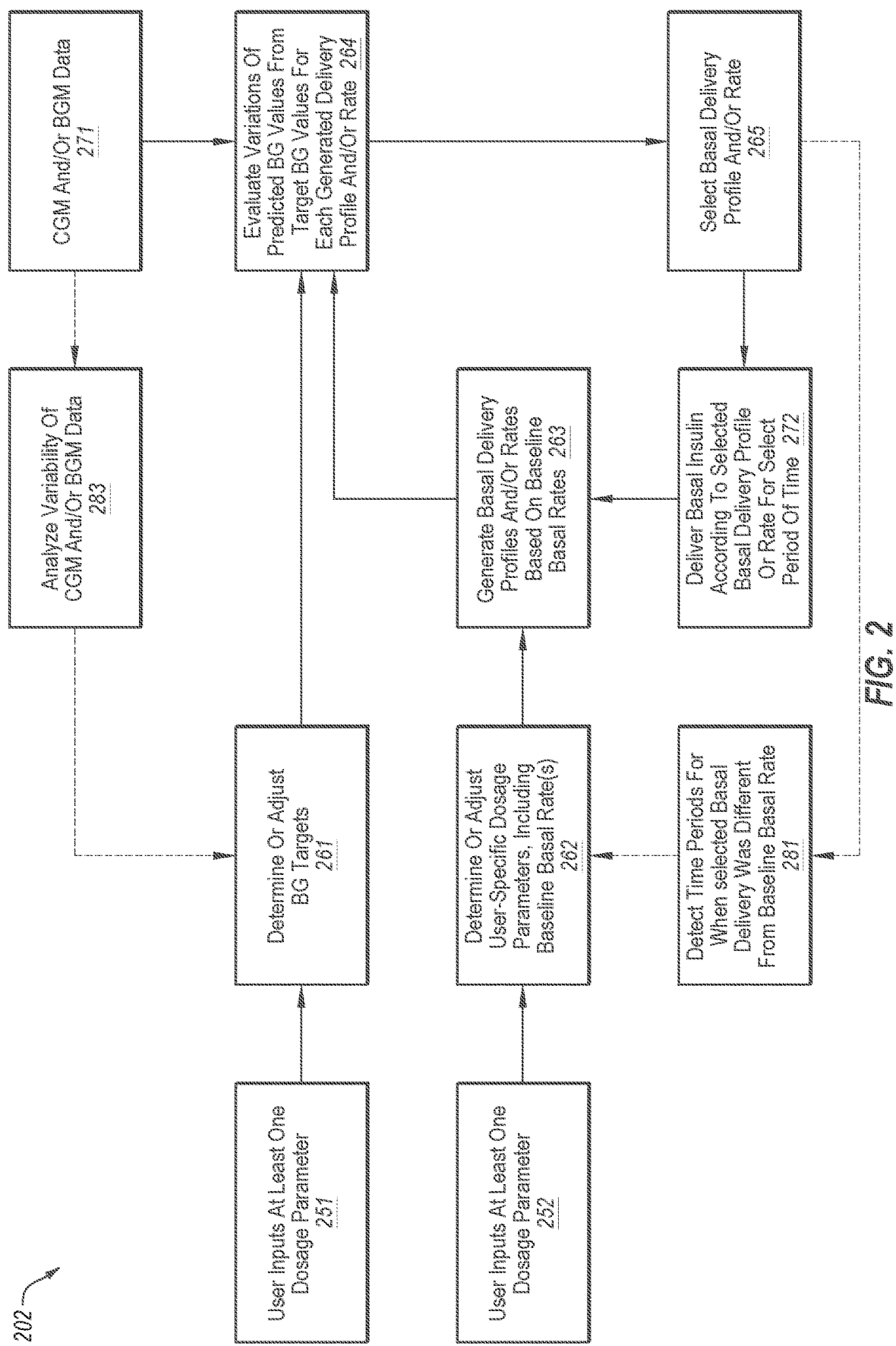
FIG. 2 is a flowchart of an example technique for adjusting basal insulin delivery rates.

FIG. 2 depicts an example method 202 for operation of a diabetes management system, such as system 10 depicted in FIG. 1. As shown in FIG. 2, a system can receive user inputs, such as user inputs at blocks 251 and 252, which can be used to provide initial settings, such as one or more target blood glucose values that may be used or determined at block 261 and/or one or more user-specific dosage parameters that may be used or determined at block 262. In some cases, user inputs at blocks 251 and 252 can be entered by a PWD, a caregiver for the PWD, or a healthcare professional. In some cases, user inputs at blocks 251 and 252 can be entered on a mobile computing device 60, such as a smartphone. Based on the user-specific dosage parameters, the method 202 can generate multiple basal insulin delivery profiles and/or rates at block 263. In some cases, the plurality of basal insulin delivery profiles and/or rates can be based upon one or more baseline basal rates. At block 264, the method 202 can analyze each basal delivery profile or rate generated at block 263 based on variations of predicted future blood glucose values from one or more target blood glucose values (such as the target blood glucose values from block 261) using blood glucose data from a continuous glucose monitor (CGM) or blood glucose meter (BGM), such as generated in block 271. In some cases, the blood glucose data can be from the continuous glucose monitor 50 from the system 10 of FIG. 1. As will be discussed below, predicted blood glucose values for each generated basal delivery profile or rate can use user-specific dosage parameters (for example, those determined or otherwise adjusted at block 262). Additionally, predicted blood glucose values can include inputs regarding previous dosages of insulin and/or food consumption (e.g., estimates of carbohydrates consumed). In some cases, predicted blood glucose values used at block 264 can consider data indicative of exercise, sickness, or any other physical state that might impact blood glucose levels in a PWD. Based on an analysis of a variation of predicted blood glucose levels performed at block 264, a basal delivery profile or rate generated at block 263 can be selected at block 265, and the system can deliver basal insulin according to that selected basal delivery profile or rate to the PWD for a select period of time at block 272. In some cases, the pump assembly 15 of system 10 of FIG. 1 can be used to deliver the insulin. In some cases, the blocks 263, 264, 265, and 272 can each be conducted by reusable pump controller 200 of system 10. In some cases, the blocks 271, 263, 264, and 265 can all be conducted by continuous glucose monitor 50 of system 10, with data regarding the selected delivery rate being sent to reusable pump controller 200. In some cases, the blocks 251, 252, 261, 262, 263, 264, and 265 can all be conducted on mobile computing device 60 of system 10 of FIG. 1, with data regarding the selected delivery rate being sent to reusable pump controller 200 from the mobile computing device 60.

Methods and systems provided herein can additionally update or adjust user-specific dosage parameters at block 262 and can update or adjust the blood glucose targets at block 261 based on the selected basal delivery profiles and/or rates selected at block 265 or based on blood glucose data obtained at block 271. In some cases, at block 281, periods of time when a selected basal delivery was different from baseline basal rate for that period of time can be detected. For these select periods of time (e.g., diurnal time segments), at block 262 the user-specific dosage parameters can be adjusted for that period of time. For example, if the selected basal delivery for a time block exceeds the baseline basal rate for that time block, at block 262 the system 10 can increase the baseline basal rate for that time block (e.g., a diurnal period) or some other related time block (such as the preceding diurnal period). For example, if the selected basal delivery from 2 PM to 3 PM exceeded the baseline basal rate for that time, the system 10 may increase the baseline basal rate for 2 PM to 3 PM or may adjust the baseline basal rate for 1 PM to 2 PM, 12 PM to 1 PM and/or 11 AM to 12 PM. In some cases, each adjustment to a baseline basal rate is less than the difference between the baseline basal rate and the selected basal delivery. In some cases, each adjustment can be a predetermined amount (e.g., baseline basal rate adjusted up or down by 0.5 unit/hour, 0.3 unit/hour, 0.1 unit per hour) or percentage (e.g., 5%, 3%, 1%), which can limit the change to the user-specific dosage parameters due to an irregular event. At block 283, the variability of blood glucose data can be analyzed to make adjustments to the blood glucose target(s) at block 261. For example, at block 283, a blood glucose data distribution can be determined for a diurnal period (e.g., between 1 AM and 2 AM) to determine a measure of dispersion of blood glucose values for the PWD during that diurnal period, and at block 261 adjustments can be made to the blood glucose target for that diurnal period, and/or adjacent periods, based on the measure of dispersion.

Each of the processes discussed in regards to FIG. 2 are discussed at further length below.

Setting Initial User-Specific Dosage Parameters

Systems and methods provided herein can use multiple user-specific dosage parameters for a PWD in order to determine rates of basal insulin delivery and optionally amounts of bolus insulin delivery. In some cases, initial user-specific dosage parameters can be set by a healthcare professional. In some cases, data entered by a user (e.g., the PWD, the PWD's caregiver, or a health care professional) can be used to estimate one or more user-specific dosage parameters. For example, FIG. 2 depicts a method where a user enters at least one dosage parameter at block 252.

In some cases, multiple user-specific dosage parameters can be set for multiple diurnal time segments. In some cases, different user-specific dosage parameters can have diurnal time segments of the same length of time or different lengths of time. In some cases, an initial setting for each user-specific dosage parameter can be set at the same value for each diurnal time segment, but the user-specific dosage parameter for each diurnal time segment can be independently adjusted in the methods and systems provided herein. In some cases, users (e.g., health care professionals) can input different user-specific dosage parameter values for different diurnal time segments.

Methods and systems provided herein can, in some cases, use user-specific dosage parameters that are commonly used in the treatment of diabetes. For example, methods and systems provided herein can ask a user to input one or more of an average Total Daily Dose (TDD) of insulin, a total daily basal (TDB) dose of insulin, an average basal rate (ABR) (which can be used as an initial baseline basal rate (BBR) in methods and systems provided herein), an insulin sensitivity factor (ISF), and/or a carbohydrate-to-insulin ratio (CR). In some cases, methods and systems provided herein can ask for a weight, age, or combination thereof of a PWD to estimate one or more user-specific dosage parameters. In some cases, methods and systems will store a BBR, an ISF, and a CR, which can each be set for multiple different time blocks over a repeating period of time (e.g., fifteen, thirty, sixty, or one hundred and twenty minute diurnal periods). As will be discussed in further detail below, methods and systems provided herein can adjust user-specific dosage parameters for each of the diurnal periods in order to personalize the delivery of insulin for the PWD in order to minimize risks for the PWD.

Methods and systems provided herein can ask for or permit a user to input a variety of different user-specific dosage parameters or dosage proxies to determine values for the initial settings of one or more user-specific dosage parameters and/or blood glucose targets. In some cases, the inputs can be limited to a Total Daily Basal (TDB) amount of insulin and a Fear of Hypoglycemia Index (FHI). In some cases, the inputs can be limited to a Total Daily Dose (TDD) amount of insulin and a FHI. In some cases, the TDB or TDD can be used determine the initial baseline basal rate (BBR), the initial carbohydrate-to-insulin ratio (CR), and the initial insulin sensitivity factor (ISF) based on mathematical relationships among and between for BBR, CR, ISF, TDB, and TDD. In some cases, a user can also set an initial ISF and CR. In some cases, a user (e.g., a health care professional) can optionally input any combination of BBR, CR, ISF, TDB, and TDD, and at least the initial BBR, initial CR, and initial ISF can be based on the values entered. For example, in some cases, a relationship between initial TDD, TDD, BBR, CR, and ISF can be expressed as follows: TDD [u/day]=2×TDB [u/day]=1800/ISF [mg/dL/u or [mmol/u]=400/CR [g/u]=48 hours/day×BBR [u/hour]. In some cases, the mathematical equation used to estimate ISF, CR, and BBR can use non-linear relationships between BBR, ISF, and CR.

Methods and systems provided herein can also make adjustments to user-entered user-specific dosage parameters prior to initial use. In some cases, methods and systems provided herein adjust user entered initial BBR, CR, and/or ISF values based on mathematical relationships among and between the initial BBR, CR, and ISF values. In some cases, if an entered ISF and an entered CR are outside of a predefined relationship between BBR, CR, and ISF, methods and systems provided herein will calculate a CR and an ISF that meets a predetermined relationship between BBR, CR, and ISF while minimizing a total change from the entered values for ISF and CR. In some cases, the predetermined relationship permits a range of CR values for each ISF value, permits a range of ISF values for each CR value, and permits a range of ISF and CR values for each BBR value. In some cases, the predetermined relationship represents a confidence interval for empirical data regarding relationships between basal rates, ISF, and CR values for a population of PWDs. In some cases, if an entered ISF, BBR, and/or CR are outside of a predefined relationship between BBR, CR, and ISF, methods and systems of the present disclosure may notify the user of the deviation from the predefined relationship. Additionally or alternatively, a healthcare provider override may be required to include ISF, BBR, and/or CR values outside of the predefined relationship as the initial user-specific dosage parameters.

Setting Initial Blood Glucose Targets

Initial blood glucose targets can be set or determined using any suitable technique. In some cases, blood glucose targets can be preprogrammed on memory within a system or device provided herein. In some cases, there can be a single blood glucose target preprogrammed into the system that does not change. In some cases, the diurnal time segments can each have a preprogrammed blood glucose target. In some cases, a user can program one or more blood glucose targets, which can be set differently for different periods of time. In some cases, a user can program the typical sleeping schedule, exercise schedule, and/or meal schedule for a PWD, and methods and systems provided herein can select lower blood glucose targets for sleep times and higher blood glucose targets around meal times and/or exercise times. In some cases, historical continuous glucose monitor data for the PWD prior to the PWD using the system can be used to set initial blood glucose targets (either for specific diurnal periods or for an entire day). In some cases, methods provided herein can have a PWD wear a CGM for a preliminary period of time (e.g., at least twenty-four hours, at least forty-eight hours, at least five days, or at least ten days) prior to allowing the methods and systems provided herein from delivering insulin at rates other than the BBR to detect blood glucose variability data for the PWD to set one or more initial blood glucose targets.

In some cases, such as shown in FIG. 2 at block 251, a user can enter a fear of hypoglycemia index (FHI), which can be used to determine and/or adjust blood glucose targets. An FHI can be represented to the user in a number of ways. In some cases, the FHI can be represented to the user as an aggressiveness index, which could be set at "prefer high," "prefer low," or "prefer moderate." In some cases, the FHI can be represented to the user as a target blood glucose level or target average blood glucose level (e.g., 100 mg/dl, 120 mg/dl, or 140 mg/dl). In some cases, the FHI can be represented to the user as a target A1C level. In some cases, the FHI can be represented to the user as a probability of going above or below a certain threshold (e.g., a five percent chance of going below 80 mg/dl, or a three percent chance of going above 200 mg/dl). In these and other cases, a user interface may be generated with an interactive feature (e.g., radio buttons, check boxes, hyperlinked images/text, drop-down list, etc.) that a user can interact with to make a selection of the FHI. In some cases, the PWD may interact with the interface to select the FHI, and in some cases, the user can be a health care professional that selects the FHI.

In some cases, each possible FHI value can correspond to a preprogrammed initial blood glucose target. For example, an FHI of "prefer high" might correspond to a preprogrammed initial blood glucose target of 140 mg/dl, an FHI of "prefer moderate" might correspond to a preprogrammed initial blood glucose target of 120 mg/dl, and an FHI of "prefer low" might correspond to a preprogrammed initial blood glucose target of 100 mg/dl. As will be discussed below, initial blood glucose targets can be adjusted over time based on data collected in methods and systems provided herein.

Modes of Operation

Methods and systems provided herein can in some cases include multiple delivery modes. In some cases, methods and systems provided herein can monitor the presence of blood glucose using one or more blood glucose measuring devices or methods, control or monitor the dispensation of insulin, and determine and/or update the user-specific dosage parameters regardless of the operating mode. For example, possible operating modes could include closed-loop or hybrid closed-loop modes that automatically adjust basal rates based on continuous glucose monitoring data (CGM) and other user-specific dosage parameters (e.g., BBR, ISF, and CR), modes that can use blood glucose monitor (BGM) data to update user-specific dosage parameters (e.g., BBRs, ISFs, and CRs) for different time blocks over longer periods of time, manual modes that require a patient to manually control the therapy program using an insulin pump, and advisory modes that recommend dosages for a user to inject using an insulin pen or syringe. By determining optimized control parameters that work across delivery modes, systems and methods provided herein can provide superior blood glucose control even when a PWD switches to a different delivery mode. For example, methods and systems provided herein may be forced to switch away from a hybrid closed-loop delivery mode that adjusts basal insulin delivery away from a BBR if a continuous glucose monitor malfunctions or the system otherwise loses access to continuous data, yet still use a personalized ISF and CR for calculating correction and/or mealtime bolus amounts. In some cases, data can be collected when the system is in an advisory or manual mode to optimize control parameters in preparation for a PWD to switch to a hybrid closed-loop system (e.g., in preparation for a PWD to start use of a continuous glucose monitor (CGM) and/or an insulin pump). In some cases, the use of a closed-loop delivery mode that adjusts basal insulin delivery away from a BBR may be prevented until a sufficient amount of current blood glucose data is available (e.g., the insulin delivery according to multiple profiles that can occur at blocks 263, 264, 265, and 272 of FIG. 2 may not occur until sufficient CGM and/or BGM data is collected at the block 271 of FIG. 2). In some cases, systems and methods provided herein can deliver insulin at the BBR rate for each diurnal period when insufficient blood glucose data is available. In some cases, methods and systems provided herein can switch between open loop and closed-loop modes based on whether there are a predetermined number of authenticated blood glucose measurements from a continuous glucose monitor within a predetermined period of time (e.g., at least two authenticated blood glucose data points within the last twenty minutes).

Automating Basal Insulin Delivery

Systems and methods provided herein can automate basal insulin delivery based on one or more stored user-specific dosage parameters (e.g., BBR, ISF, CR), one or more blood glucose targets, and/or blood glucose data. The example method depicted in FIG. 2 depicts an example process of automating basal insulin delivery as blocks 263, 264, 265, and 272. Methods and systems provided herein can use a model predictive control system that projects multiple future blood glucose levels for a future time period for multiple possible basal insulin delivery profiles and/or rates over that future time period and determines which of the multiple possible basal insulin delivery profiles and/or rates will produce future blood glucose values that approximate one or more blood glucose targets. Methods and systems provided herein can produce improved control as compared to control algorithms that merely make adjustments to basal insulin delivery without evaluating multiple possible basal insulin delivery profiles or rates. In some cases, methods and systems provided herein can predict future blood glucose values at least two hours, or at least three hours, or at least four hours, or at least five hours into the future, which can adequately consider the long term impact of increasing or decreasing the basal insulin delivery relative to the BBR. After a rate or profile is selected, the rate or profile can be delivered for a predetermined delivery period of time (for example, the block 272 of FIG. 2) prior to repeating one or more of the steps in the process of selecting a new basal insulin delivery profile or rate. In some cases, this predetermined delivery period of time can be less than the length of time for the generated basal insulin delivery profiles and/or rates and less than the time period for which future blood glucose values were estimated, thus methods and systems provided herein can dynamically make changes to basal insulin delivery based on recent blood glucose data. For example, generating basal delivery profiles at block 263 may be repeated every fifteen minutes, and the period of time evaluated at block 264 may be a four hour window such that every fifteen minutes, a new four hour window of analysis for the basal delivery profiles is generated. In this way, each delivery action is based on a prediction not only of that action, but on how the prior delivery action is determined to impact blood glucose levels for four hours into the future.

Generating Possible Basal Delivery Profiles and/or Rates for Evaluation

Figure 3:
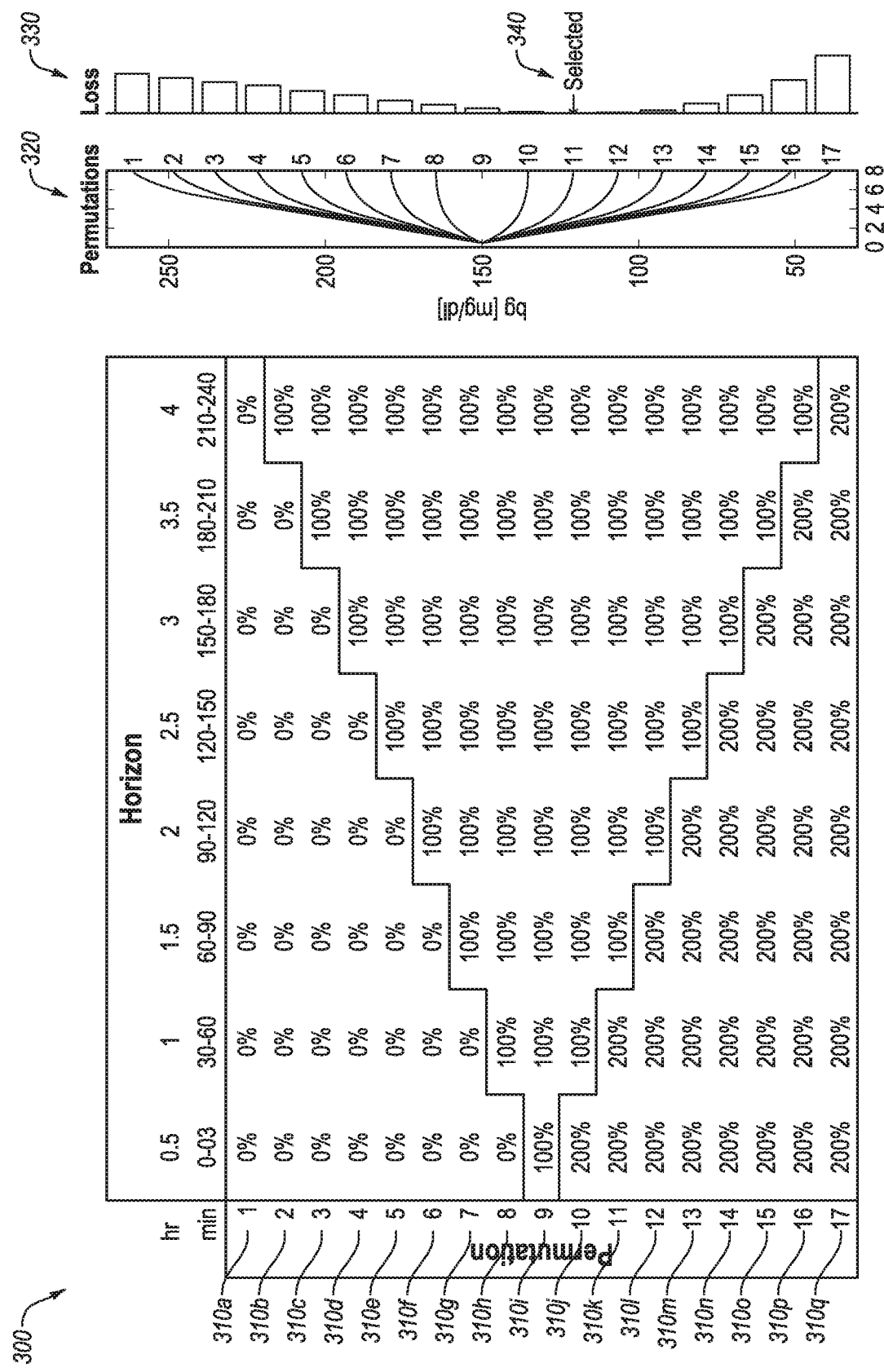
FIG. 3 illustrates multiple example insulin delivery profiles, projected blood glucose levels for the profiles, and a "loss" calculation for each profile.

FIG. 3 illustrates an example chart 300 of delivery profiles 310a-310q over a four hour time horizon. FIG. 3 also includes a graph 320 illustrating the projected effect of the profiles 310a-310q on blood glucose levels, and a graph 330 illustrating an accumulation of variations from a target blood glucose level (e.g., loss) using a cost function.

Possible basal insulin delivery profiles and/or rates can be generated using any suitable technique. In some cases, each generated profile or rate can be based on user-specific dosage parameters. In some cases, each generated profile or rate can be based on one or more user-specific dosage parameters that are specific to a particular diurnal period. In some cases, each generated profile or rate is based on a predetermined relationship to a stored baseline basal rate (BBR), such as indicated at block 263 in FIG. 2. In some cases, generated profiles and/or rates for analysis extend for at least two hours, at least three hours, or for at least four hours. In some cases, the generated profiles may extend for a day (e.g., twenty-four hours) or less. In some cases, each generated profile or rate includes basal insulin delivery rates based on predetermined multiples or fractions of one or more stored BBRs. In some cases, multiple insulin delivery profiles and/or rates are based on multiple diurnal-time-block-specific BBRs. In some cases, generated basal insulin delivery profiles each deliver insulin at a ratio of a BBR, such as an integer multiple of one or more stored BBRs (e.g., 0×BBR, 1×BBR, 2×BBR, and 3×BBR). In some cases, insulin delivery profiles can delivery insulin at ratios that may include both fractions and multiples of one or more stored BBRs (e.g., 0×BBR, 0.5×BBR, 1×BBR, 1.5×BBR, and 2×BBR). In some cases, generated basal insulin delivery profiles each deliver insulin at only multiples or fractions of between 0 and 3. In some cases, generated basal insulin delivery profiles each deliver insulin at only multiples or fractions of between 0 and 2. In some cases, such as shown in FIG. 3, multiple generated basal delivery profiles can include only deliveries of basal insulin at 0% of BBR, 100% of BBR, or 200% of BBR. In some cases, each generated basal delivery profile permutation has fixed future time periods. In some cases, different future time periods for permutations can have different lengths. In some cases, the number of generated basal delivery profiles or rates for evaluation is less than 100, less than 50, less than 30, less than 25, or less than 20. By limiting the number of evaluated preset permutations based on stored BBRs, methods and systems provided herein can limit an energy expenditure used to run a controller determining a basal delivery rate.

In some cases, one or more of the profiles 310a-310q may include an inflection point between a first insulin delivery amount for a first portion of delivery actions and a second delivery amount for a second portion of delivery actions. For example, the profile 310b may include an inflection point between 0% and 100% between 3.5 hours and 4 hours (e.g., for the portion before the inflection point, 0% of the BBR is delivered as the delivery action and for the portion after the inflection point, 100% of the BBR is delivered as the delivery action). As another example, the profile 310k may include an inflection point between 100% and 200% between 1 hour and 1.5 hours (e.g., before the inflection point, 100% of the BBR is delivered as the delivery action and after the inflection point, 200% of the BBR is delivered as the delivery action). In some cases, such as illustrated in FIG. 3, each profile may be a permutation of including one inflection point (or no inflection point) between three possible delivery actions (e.g., 0%, 100%, 200%), yielding seventeen profiles for a four hour window of projection. In some cases, more than one inflection point may be used, yielding additional profiles. In some cases, the number of profiles may be fewer than thirty. In some cases, only three profiles are analyzed (e.g., profiles 8, 9, and 10 of FIG. 3, 310h-j) in order to select between whether to delivery 0%, 100%, or 200%. In some cases, the inclusion of additional profiles assuming no basal insulin (e.g., profile 1, 310a) or continuing supply of maximum basal insulin (e.g., 17, 310q) can allow the system to detect an approaching predicted hypoglycemic event or an approaching predicted hyperglycemic event, and additional profiles (e.g., 2-7 & 11-16) can be selected and recorded to detect situations where future decisions are not conforming to an expected profile. In some cases, methods and systems provided herein can continue to deliver insulin according to a selected profile after the select period of time in block 272, including changes in basal delivery rates, if reliable up-to-date blood glucose data is lost. In other cases, methods and systems provided herein will revert to another mode or alarm and stop insulin delivery if reliable up-to-date blood glucose data is lost.

In some cases, the range of possible values of the BBR for a given profile can be adjusted or modified depending on the FHI. For example, in some cases, if the FHI is "prefer low" (e.g., indicating a preference for the system to aggressively keep the PWD within range and not go high), the target blood glucose might be set around 100 mg/dl and the range for delivery may include 0%, 50%, 100%, 200%, and 300% BBR. As another example, if the FHI is "prefer high" (e.g., indicating that the PWD prefers to avoid hypoglycemic events even with a higher risk of hyperglycemic events), the target blood glucose might be set around 140 mg/dl and the range for delivery may include 0%, 100%, and 200% of BBR.

Evaluating Generated Basal Delivery Profiles and/or Rates

Referring again to FIG. 2 and FIG. 3, the evaluation of multiple generated basal insulin delivery profiles and/or rates includes projecting future blood glucose levels and comparing those to blood glucose targets. In some cases, multiple permutations may be generated and analyzed. FIG. 3 depicts possible projections for each permutation of insulin delivery depicted in FIG. 3.

Predicting Future Blood Glucose Values

Systems and methods provided herein can use any suitable physiology model to predict future blood glucose values. In some cases, methods and systems provided herein can predict future blood glucose values using past and current carbohydrate, insulin, and blood glucose values.

Figure 4:
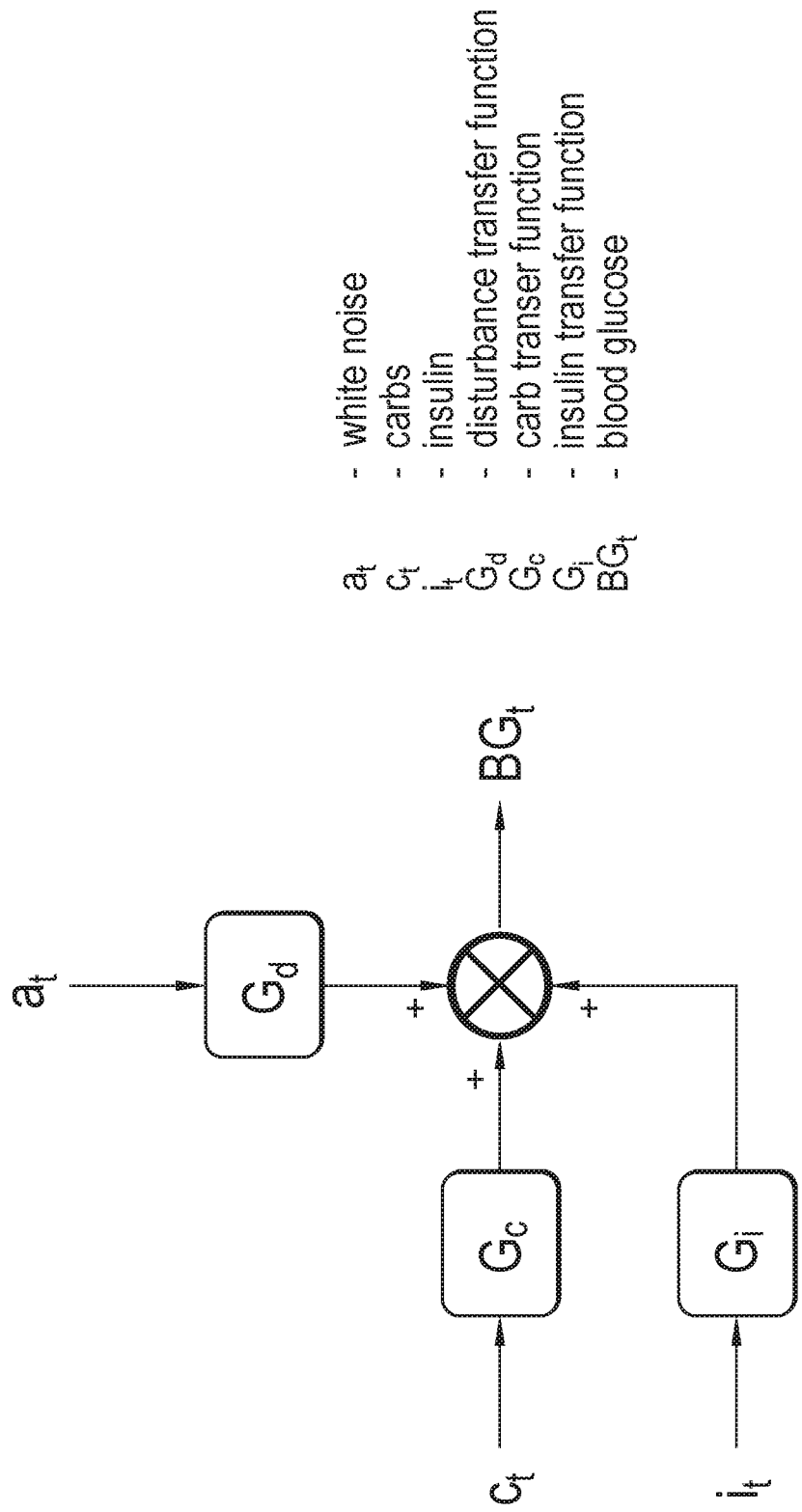
FIG. 4 illustrates an example model for calculating future blood glucose values.

Systems and methods provided herein can in some cases estimate a first future blood glucose a model as depicted in FIG. 4. In some cases, blood glucose can be approximated using two determinist Integrating first order plus dead time (FOPDT) models for the effect of carbohydrates and insulin, combined with an autoregressive (AR2) disturbance model. Accordingly, blood glucose (BG) at time (t) can be estimated using the following equation:

$$BG_t = y_t = BGc_t + BGi_t + BGd_t = G_c c_t + G_i i_t + G_d e^{\alpha t}$$

From the equation above, the first element may represent the effect on blood glucose due to carbohydrates:

$$G_c = \frac{K_c(1-\alpha_c)B^{c_{dt}}}{(1-\alpha_c B)(1-B)}.$$

where:

B is the backward shift operator such that $B\gamma_t = \gamma_{t-1}$, $B^2\gamma_t = \gamma_{t-2}$, $B^k\gamma_t = \gamma_t = \gamma_{t-k}$ $$k_c = \frac{ISF}{CR}$$

is the carb gain (in units of mg/dl/g)

$$\alpha_c = e^{-\frac{ts}{\tau_c}},$$

where $\tau_c$ is the carb time constant (for example, approximately 30 min), and where ts is the sampling time (for example, a CGM may use a sampling time interval of every 5 min)

$c_{dt}$=floor($\tau_{dc}$/ts), where $\tau_{dc}$ is the carb deadtime (for example, approximately 15 min) From the equation above, the second element may represent the effect on blood glucose due to insulin:

$$G_i = \frac{K_i(1-\alpha_c)B^{i_{dt}}}{(1-\alpha_i B)(1-B)}.$$

where:

$k_i$=−ISF is the insulin gain (in units of mg/dl/unit)

$$\alpha_i = e^{-\frac{ts}{\tau_i}},$$

where $\tau_i$ is the insulin time constant (for example, approximately 120 min)

$i_{dt}$=floor($\tau_{ch}$/ts), where $\tau_{di}$ is the insulin deadtime (for example, approximately 30 min) From the equation above, the third element may represent the effect on blood glucose due to disturbances (e.g., the AR2 disturbance model):

$$G_d e^{\alpha t}$$

and may be based on the following log-transformed AR2 model:

$$\ln\left(\frac{BGD_t}{\mu^*}\right) = \alpha_1 \ln\left(\frac{BGD_t}{\mu^*}\right) + \alpha_2 \ln\left(\frac{BGD_{t-2}}{\mu^*}\right) + \alpha_t$$

which when rearranged, yields:

$$BGd_t = BGd_{t-1}^{\alpha_1} BGd_{t-2}^{\alpha_2} \mu^{*(1-\alpha_1-\alpha_2)} e^{\alpha_t}$$

where, in some examples, $$a_t \sim \text{Normal}(0, \sigma_a)$$

and $$\sigma_a \approx 50\% \ln(\sigma^*)\sqrt{\frac{1+\alpha_2}{1-\alpha_2}((1-\alpha_2)^2) - \alpha_1^2)}$$

with $\mu^* \cdot 10^{Normal\,(2.09,\,0.08)}$ and $\sigma^* \cdot 10^{Normal\,(0.15,\,0.028)}$ such that $\alpha_1 \approx 1.6442$, $\alpha_2 \approx 0.6493$.

Using the above notation, expansion of the initial equation for $BG_t$ may be represented by the equation:

$$BG_t = \frac{k_c(1-\alpha_c)}{(1-\alpha_c B)(1-B)} c_{t-dt_c} + \frac{k_i(1-\alpha_i)}{(1-\alpha_i B)(1-B)} i_{t-dt_i} + BGd_{t-1}^{\alpha_1} BGd_{t-2}^{\alpha_2} \mu^{*(1-\alpha_1-\alpha_2)}$$

Systems and methods provided herein can in some cases calculate an amount of insulin on board (IOB) and/or an amount of carbohydrates on board (COB) in order to predict future blood glucose values. IOB and COB represent the amount of insulin and carbohydrates, respectively, which have been infused and/or consumed but not yet metabolized. Knowledge of IOB and COB can be useful for a user of a method or system provided herein when it comes to bolus decisions to prevent insulin stacking, but knowledge of IOB and COB can also be used in methods and systems provided herein to predict future blood glucose values.

IOB and COB represent the amount of insulin and carbohydrates, respectively, which have been infused and/or consumed but not yet metabolized. Knowledge of IOB can be useful in correcting bolus decisions to prevent insulin stacking. Knowledge of IOB and COB can be useful for predicting and controlling blood glucose. Both insulin infusion and carbohydrate consumption can involve deadtime or transportation delay (e.g., it can take ten to forty minutes for insulin and/or carbohydrates to begin to affect blood glucose). During the period immediately after entering the body (e.g., during the deadtime period), it can be beneficial to account for IOB and COB in any decisions such as bolusing. This can be called "Decision" IOB/COB. "Action" IOB/COB, on the other hand, can represent the insulin and/or carbohydrates available for action on blood glucose. In some cases, Decision IOB can be a displayed IOB, while Action IOB can be an IOB determined for use in selecting a basal delivery rate or profile in methods and systems provided herein.

From the equations above, $$BG_{it} = \frac{-ISF(1-\alpha_i)B^{i dt}}{(1-\alpha_i B)(1-B)} i_{t-i_{dt}}$$

where $BY_t = Y_{t-1}$, $B^2 Y_t = Y_{t-2}$, $B^k Y_t = Y_{t-k}$ $$\alpha_i = e^{-\frac{ts}{\tau_i}}$$

where $\tau_i$ is the insulin time constant (for example, approximately 120 min) $i_{dt}$=floor($\tau_{di}$/ts), where $\tau_{di}$ is the insulin deadtime (for example, approximately 30 min) and where $\tau_s$ is the sampling time (for example, a CGM may use a sampling time interval of every 5 min)

"Decision" IOB

In some embodiments, Decision IOB at time (t) (IOB Dt) may be calculated according to the following mathematical process:

$$IOB\_D_t = IOB\_D_{t-1} - \frac{BG_{i_t} - BG_{i_{t-1}}}{-ISF} + i_t$$

or, alternatively, $$\nabla IOB\_D_t = -\frac{1-\alpha_i}{1-\alpha_i B} i_{t-i_{dt}} + i_t$$

substituting the equation above for Bat into the equation for IOB_$D_t$ or $\nabla$IOB_$D_t$ yields $$IOB\_D_{D_t} = \frac{1-\alpha_i B - (1-\alpha_i)B^i\, dt}{1-(\alpha_i+1)B + \alpha_i B^2} i_t$$

or, alternatively, $$\nabla IOB\_D_t = -\frac{\nabla BG_{i_t}}{-ISF} + i_t$$

"Action" IOB

In some embodiments, Action IOB at time (t) (IOB_$A_t$) may be calculated according to the following mathematical process:

$$IOB\_A_t = \frac{1}{1-\alpha_i B} i_{t-i_{dt}}$$

For an arbitrary series of insulin infusions, using an infinite series of expansions of $$\frac{1}{1-\alpha_i B},$$

IOB_$A_t$ may be represented by $$IOB_{A_t} = \sum_{k=0}^{n} \alpha_i^k i_{t-k-i_{dt}}$$

Stated another way, $$BG_{i_t} = \frac{-ISF(1-\alpha_i)}{1-B} IOB\_A_t$$

The formulas for COB, including Action COB and Decision COB, may be developed in a similar fashion, using the equation above related to $G_c$:

$$G_{ct} = \frac{k_c(1-\alpha_c)B^c\, dt}{(1-\alpha_c B)(1-B)}$$

Accordingly, future blood glucose data can be estimated using current or recent blood glucose data, data about when carbohydrates were consumed, and/or data regarding when insulin was and/or will be administered. Moreover, because evaluated insulin delivery profiles and/or rates include basal insulin delivery rates above and below the BBR, those insulin delivery rates above BBR can be added to the IOB calculation and insulin delivery rates below the BBR can be subtracted from the IOB. In some cases, a variation in a Decision IOB due to actual variations from BBR can be limited to positive deviations in order to prevent a user from entering an excessive bolus.

Estimating Glucose Levels from Blood Glucose Data

Referring back to FIG. 1, continuous glucose monitor 50 and blood glucose meter 70 can both provide blood glucose data to system 10. The blood glucose data, however, can be inaccurate. In some cases, continuous glucose monitor 50 can be replaced (or have sensor shaft 56 replaced) at regular or irregular intervals (e.g., every three days, every five days, every seven days, or every ten days). In some cases, data from blood glucose meter 70 can be used to calibrate the continuous glucose monitor 50 at regular or irregular intervals (e.g., every three hours, every six hours, every twelve hours, every day, etc.). In some cases, systems and methods provided herein can remind a user to change the continuous glucose monitor 50 or calibrate continuous glucose monitor 50 using blood glucose meter 70 based on data from continuous glucose monitor 50 and/or at regular intervals. For example, if the pattern of insulin delivery varies greatly from an earlier predicted pattern of insulin deliveries may indicate that the continuous glucose monitor 50 requires maintenance and/or replacement.

In some cases, methods and systems can determine an accuracy factor for blood glucose data from the continuous glucose monitor 50 based upon when the particular continuous glucose monitor sensor shaft 56 was first applied to the PWD and/or when the particular continuous glucose monitor 50 was last calibrated using blood glucose data from blood glucose meter 70. In some cases, methods and systems provided herein make adjustments to future blood glucose targets based on a calculated accuracy factor for data from the continuous glucose monitor 50 in order to reduce a risk of hypoglycemia. In some cases, methods and systems provided herein can estimate the current blood glucose level as being a predetermined number of standard deviations (e.g., 0.5 standard deviations, one standard deviation, two standard deviations) below data received from continuous glucose monitor 50 based on the accuracy factor in order to reduce a risk of hypoglycemia.

After continuous glucose monitor 50 is calibrated or replaced with a new continuous glucose monitor or has a new sensor shaft 56 installed, however, a discontinuity of reported glucose data from the continuous glucose monitor 50 can occur. In some cases, methods and systems provided herein, however, can use and report historical blood glucose values in selecting insulin basal rates and/or profiles. In some cases, methods and systems provided herein can revise stored and/or reported blood glucose levels based on data from one or more continuous glucose monitors in order to transition between different continuous glucose monitor sensors and/or to data produced after a calibration. In some cases, a continuous glucose monitor 50 can provide each blood glucose value with an estimated rate of change, and the rate of change information can be used to retrospectively adjust one or more historical estimated blood glucose values from data from a continuous glucose monitor 50. For example, the rate of change of the pre-calibration reported blood glucose value may be used to determine an estimated post-calibration value assuming the same rate of change. A ratio of the post-calibration reported blood glucose value to the estimated post-calibration value can then be used to linearly interpolate multiple historical blood glucose values based on that ratio. In some cases, all readings between calibrations can be linearly interpolated. In some cases, data from a predetermined amount of time prior to a calibration can be linearly interpolated (e.g., fifteen minutes, thirty minutes, one hour, two hours, three hours, or six hours).

Analyzing Variations from Targets

Methods and systems provided herein can evaluate each future basal delivery profile by predicting blood glucose for the basal delivery profiles (e.g., as illustrated in the graph 320 of FIG. 3) and calculating a variation index of the predicted blood glucose values from the target blood glucose values. Methods and systems provided herein can then select the profile of basal rate delivery actions that corresponds to the lowest variation index (e.g., the lowest value 340 of the graph 330 of FIG. 3). The variation index can use a variety of different mathematical formulas to weight different types of variations. The variation index can be a cost function. In some cases, methods and systems provided herein can use a cost function that sums up squares of differences for the projected blood glucose values from target blood glucose values for multiple diurnal time segments. Methods and systems provided herein can use any suitable cost function. In some cases, cost functions can sum the absolute value of the difference between each predicted blood glucose value and each blood glucose target. In some cases, cost functions used in methods and systems provided herein can use a square of the difference. In some cases, cost functions used in methods and systems provided herein can use a square of the difference between the logs of each predicted blood glucose level and each corresponding blood glucose target. In some cases, cost functions used in methods and systems provided herein can assign a higher cost to blood glucose values below the blood glucose target in order reduce the risk of a hypoglycemic event. FIG. 3 depicts the "loss" (i.e., the resulting value for a cost function) for the plurality of basal delivery profiles. As shown in FIG. 3, the basal delivery profile 11, 310*k*, corresponds to the lowest value 340. In some cases, a profile that has the lowest value of loss may be selected. In some cases, cost functions provided herein can include elements that additional bias the selected profile toward a profile that maintains the previously administered basal rate and/or that delivers the baseline basal rate, which may prevent the system from changing delivery rates every time a basal delivery profile or rate is selected in Block 265. In some cases, the cost function can square the difference between the log of the values in order to provide a higher cost for projected lows than projected highs.

Selecting a Basal Insulin Delivery Profile or Rate

Methods and systems provided herein can then select a basal profile or rate that produces the lowest cost function value. As shown in FIG. 3, the delivery profile 11, 310*k*, has the lowest loss, and is thus the selected profile for delivery. With reference to FIG. 2, at block 272 insulin can then be delivered according to the selected profile for an amount of time. In some cases, the amount of time is a predetermined amount of time. In some cases, the predetermined amount of time is less than the time horizon for the estimated future blood glucose values and the length of time for the selected basal delivery profile. In some cases, the predetermined amount of time is ninety minutes or less, sixty minutes or less, forty-five minutes or less, thirty minutes or less, twenty minutes or less, fifteen minutes or less, ten minutes or less, or five minutes or less. After the period of time, the system can again repeat the operations at blocks 263, 264, 265, and 272 to select and deliver a basal insulin for a subsequent period of time.

Adjusting User-Specific Dosage Parameters

Methods and systems provided herein can make adjustments to the user-specific dosage parameters. For example, FIG. 2 includes the block 281 for detecting time periods when an amount of delivered basal insulin is different from a BBR, which can then be used to adjust user-specific dosage parameters at block 262. These updated user-specific dosage parameters can then be used to generate new basal delivery profiles at block 263 and used at block 264 to evaluate different basal delivery profiles. For example, for a BBR of 1.46 U/hour (associated with a TDB of 35 U/day), if a diurnal period under consideration is one hour and for the first forty-five minutes, insulin was delivered at a rate of 2.92 U/hour (e.g., 2× the BBR) and only the last fifteen minutes was delivered at a rate of 1.46 U/hour (e.g., 1× the BBR), user-specific dosage parameters for a related diurnal time period (e.g., that same hour on another day in the future, or a preceding diurnal time period on a day in the future) may be adjusted.

In some cases, methods and systems provided herein can make adjustments for BBR, ISF, and/or CR for multiple diurnal periods based on variations in the insulin amounts actually delivered for that diurnal period compared to the baseline basal insulin rate for that diurnal period. In some cases, diurnal periods can have a same length of time as a predetermined length of time for the delivery of a selected insulin delivery. In some cases, a diurnal period can be greater than a predetermined length of time for the delivery of a selected insulin delivery, for example, multiple doses of insulin may be delivered during a single diurnal period. In some cases, a diurnal period can be fifteen minutes, thirty minutes, one hour, two hours, etc. In some cases, an actual delivery of insulin for a diurnal period must surpass a predetermined threshold above or below the BBR for that diurnal period in order for user-specific dosage parameters (e.g., BBR, ISF, CR) to be adjusted for that diurnal period. For example, diurnal periods can be one hour long, but each basal delivery profile can be delivered for fifteen minute time periods before methods and systems provided herein determine a new basal insulin delivery profile, and methods and systems provided herein can require that the total basal insulin delivery for the diurnal period be at least greater than 50% of the BBR to increase the BBR for that diurnal period or at 50% or less than the BBR to decrease the BBR for that diurnal period. Using the example from above, for a BBR of 1.46 U/hour, if a diurnal period under consideration is one hour and for the first forty-five minutes (e.g., three iterations of profile generation and delivery actions), insulin was delivered at a rate of 2.92 U/hour (e.g., 2× the BBR) and only the last fifteen minutes (e.g., one iteration of profile generation and delivery action) was delivered at a rate of 1.46 U/hour (e.g., 1× the BBR), the total amount delivered would be at 175% of the BBR for the one hour diurnal period, or an average ratio of 1.75× the BBR. In some cases, because the 175% exceeded 150% of the BBR, methods and systems of the present disclosure may adjust user-specific dosage parameters. As another example using the same 1.46 U/hour BBR and a two hour diurnal time period and delivery profiles reformulated every fifteen minutes, if the first forty-five minutes delivered no insulin (0× the BBR) and the last hour and fifteen minutes delivered 1.46 U/hour, the total amount delivered may be 62.5% of the BBR, or 0.625× of the BBR. In some cases, because the 62.5% did not drop below 50% of the BBR, methods and systems of the present disclosure may not adjust the user-specific dosage parameters and may maintain the user-specific dosage parameters for the particular diurnal period.

An adjustment to the CR, ISF, and BBR can be any suitable amount. In some cases, the adjustment to the BBR is less than the difference between the delivered basal insulin and the previously programmed BBR. In some cases, a change to each user-specific dosage parameter (e.g., BBR, ISF, and CR) is at a predetermined percentage or value. For example, in some cases, each of BBR and ISF can be increased by 5%, 3%, or 1% and CR decreased by the same percent for every period where the amount of delivered basal insulin exceeds the BBR by at least 25%. In some cases, BBR and ISF can be decreased by 5%, 3%, or 1% and CR increased by the same percent for every period where the amount of delivered basal insulin exceeds the BBR by at least 25%. By setting each adjustment at a low level, methods and systems provided herein can eventually be personalized for the PWD without over adjusting the system based on an unusual day (e.g., to mitigate the risk of short term disturbances being mistaken for changes in physiological parameters). In some cases, the adjustment to CR, ISF, and BBR may be based on a relationship between CR, ISF, and BBR, rather than a fixed amount or percentage. In some cases, CR, ISF, and BBR can be adjusted based on a predetermined relationship between their log-transformed values. In some cases, the adjustments to CR, ISF, and BBR may be performed independently. In these and other cases, systems and methods provided herein can monitor for variations in adjustments to CR, ISF, and/or BBR away from a relationship between CR, ISF, and BBR. In such cases, a notification may be provided to a user (e.g., the PWD or a health care provider) that the systems and methods of the present disclosure had adjusted one or more user-specific dosage guidelines outside of or away from a relationship between CR, ISF, and BBR.

In some cases, systems and methods provided herein can update or adjust user-specific operating parameters for select time blocks every twenty-four hours. In some cases, diurnal periods can be updated dynamically (e.g., immediately after a basal delivery profile or rate is selected). In some cases, diurnal periods can be updated by reusable pump controller 200, by mobile computing device 60, or using a remote server in the cloud. In some cases, the length of diurnal periods can vary depending on the time of day (e.g., nighttime diurnal periods could be longer) or depending on the user-specific dosage parameter (e.g., BBRs might have fifteen minute diurnal periods while the CR and ISF might have one hour diurnal periods).

In some cases, when performing an adjustment, a related diurnal period may be adjusted based on variation from the BBR for a given diurnal period. For example, if an adjustment were to be performed because delivery from 2 PM to 3 PM exceeded 150% of the BBR, an adjustment may be made to the user-specific dosage parameters for the same time on a different day in the future (e.g., 2 PM to 3 PM on the next day) or a preceding diurnal period on a different day in the future (e.g., 1 PM to 2 PM on the next day or 12 PM to 1 PM on the next day, etc.). In some cases, modifying a preceding diurnal period may adjust more appropriately for variations in BBR and/or other user-specific dosage parameters because of the delay of effect after delivery of insulin and/or the delay of effect after consumption of carbohydrates (e.g., if a PWD repeatedly goes high between 2 PM and 3 PM, the PWD may need additional insulin during the 1 PM to 2 PM hour).

In some cases, systems and methods disclosed herein can smooth adjustments to user-specific dosage parameters in one diurnal period relative to other diurnal periods. For example, in some cases, a proposed adjustment to a BBR for a first diurnal period may be compared to one or more preceding diurnal periods and one or more following diurnal periods. If the proposed adjustment is a threshold amount different from one or more of the preceding or following diurnal period values, the proposed adjustment may be modified to avoid drastic jumps between diurnal periods. For example, if a preceding diurnal period had a BBR of 1.06 U/hour and the proposed adjustment was from a BBR of 1.4 U/hour to a BBR of 1.90 U/hour, the adjustment may be reduced to smooth the transition from the preceding diurnal time period. In some cases, the smoothing may include adjusting preceding or following diurnal time periods in addition to the diurnal time period under consideration. In these and other cases, such adjustment may be performed once per day or at another periodic time such that following diurnal periods may have already occurred and the smoothing is not being performed based on projections. For example, the diurnal period from 1 PM to 2 PM may be analyzed for potential adjustment at 4 PM such that the diurnal periods from 11 AM to 12 PM and 12 PM to 1 PM and from 2 PM to 3 PM and 3 PM and 4 PM are available in considering any adjustment and/or smoothing to perform on the user-specific dosage parameters for the 1 PM to 2 PM diurnal period.

In some cases, systems and methods disclosed herein can adjust user-specific dosage parameters in a diurnal period based on the FHI. For example, if the FHI is high (e.g., indicating a preference that the PWD not go low), the range for adjusting the BBR may be limited to a relatively small change (e.g., 0.5%, 1%, 1.5%, etc.). As another example, if the FHI is low (e.g., indicating that the PWD is not as concerned about going low), the range for adjusting the BBR may include a broader range of changes (e.g., up to a 5% change).

Adjusting Blood Glucose Targets

Methods and systems provided herein can make adjustments to the blood glucose targets. For example, FIG. 2 includes the block 283 for analyzing the variability of CGM and/or BGM data (e.g., data from the CGM 50 and/or the BGM 70 of FIG. 1), which can then be used to adjust blood glucose targets at the block 261. In some cases, blood glucose targets are set for diurnal periods. In some cases, the diurnal periods for blood glucose targets are at least fifteen minutes long, at least thirty minutes long, at least one hour long, or at least two hours long. In some cases, blood glucose targets can have a constrained range. In some cases, blood glucose targets must be at least 80 mg/dL, at least 90 mg/dL, at least 100 mg/dL, at least 110 mg/dL, or at least 120 mg/dL. In some cases, blood glucose targets must be no greater than 200 mg/dL, no greater than 180 mg/dL, no greater than 160 mg/dL, no greater than 140 mg/dL, or no greater than 125 mg/dL. In some cases, a constrained range is between 100 mg/dL and 160 mg/dL. These updated blood glucose targets can then be used at block 264 to evaluate different basal delivery profiles.

Updated blood glucose targets for a particular diurnal period can be based on historical blood glucose patterns for the PWD and the risk of hypoglycemia for the PWD over the course of a day. The updated blood glucose targets can also consider a set FHI. For example, based on an FHI selection, an initial blood glucose target at a conservative level (e.g. 120 mg/dl) can be set, and over the course of a period of days and/or weeks as more information is gained about variability patterns, the blood glucose target(s) can be adjusted. A slow adjustment can prevent the blocks 283 and 261 from overreacting to short term disturbances but still allow blood glucose target individualization to a PWD's lifestyle and habits over time.

In some cases, methods and systems provided herein can also allow a user to temporarily or permanently adjust blood glucose targets by adjusting their fear of hypoglycemia index (FHI). In some cases, a user adjustment to FHI can result in blood glucose targets being temporarily or permanently adjusted to blood glucose targets based on the variability of CGM (and optionally BGM) data for multiple diurnal periods. In some cases, a user adjustment to FHI can add or subtract a predetermined value from a previously used blood glucose target (e.g., an adjustment from "prefer low" to "prefer medium" could add 20 mg/dL to each stored blood glucose target). In some cases, a temporary adjustment to FHI could analyze variability data for multiple time blocks and set a new blood glucose target for each diurnal period based on the variability data for that time block (e.g., an adjustment from "prefer low" to "prefer medium" could adjust the blood glucose target for each diurnal period from a level estimated to send the PWD below a threshold of 70 mg/dL about 5% of the time to a level estimated to send the PWD below a threshold of 70 mg/dL about 3% of the time).

Allowing a PWD to change the FHI for temporary time periods or otherwise use some form of temporary override may allow a PWD to tell the system that the PWD is about to or is experiencing some activity or condition that might impact their blood glucose levels. For example, a PWD that is about to exercise might set a temporary FHI of "prefer high" to offset the risk that exercise will send the PWD low for that period of time. In some cases, a PWD might set a temporary FHI of "prefer low" if the PWD is feeling sick in order to offset the risk that the sickness will result in high blood glucose levels. In some embodiments, such a temporary override may be a separate setting or entry other than the FHI. In these and other cases, in addition to a preferred range (e.g., "high" or "low"), the user may be able to select a temporary override of a target blood glucose level or range (e.g., approximately 120 mg/dL or between 120 mg/dL and 200 mg/dL, etc.), or may select a particular activity or circumstance the PWD will participate in or is experiencing (e.g., exercising, sickness, menses, driving, etc.).

In some cases, after a temporary override is input, methods and systems of the present disclosure can select a new profile to follow based on the profile more closely aligning with the temporary override. In these and other cases, a new set of profiles can be generated before selecting the new profile. Additionally or alternatively, after a temporary override is input, methods and systems of the present disclosure can temporarily modify the BBR. In some cases, after the BBR has been modified, a new set of profiles may be generated based on the temporarily modified BBR.

In some cases, a log of temporary overrides can be generated. For example, each time a user (e.g., the PWD) inputs an override, an entry can be created in the log that includes what override was selected, what starting and ending times, and/or what the reason for the override was. In these and other cases, the log can be periodically provided to a healthcare professional, for example, via email or some other electronic message. Additionally or alternatively, in some cases, the log can be parsed for patterns. For example, the PWD may input a temporary override every Monday, Wednesday, and Friday from 6 PM to 7 PM when the PWD exercises. The log can be parsed to find such patterns of overrides. In these and other cases, methods and systems of the present disclosure can modify a BBR based on the patterns. Continuing the example, the BBR may be lowered for the diurnal period of 6 PM to 7 PM on Monday, Wednesday, and Friday because of a PWD repeatedly entering a temporary override during that diurnal period that the PWD is exercising and not to go low.

Overall System

Methods and systems provided herein can control basal insulin delivery over time and adjust basal user-specific dosage parameters and blood glucose targets for multiple diurnal periods to personalize the user-specific dosage parameters over time. For example, FIG. 5 illustrates various examples of user interfaces (e.g., 400, 410, 420, and 430) displaying various aspects of the present disclosure.

Figure 5:
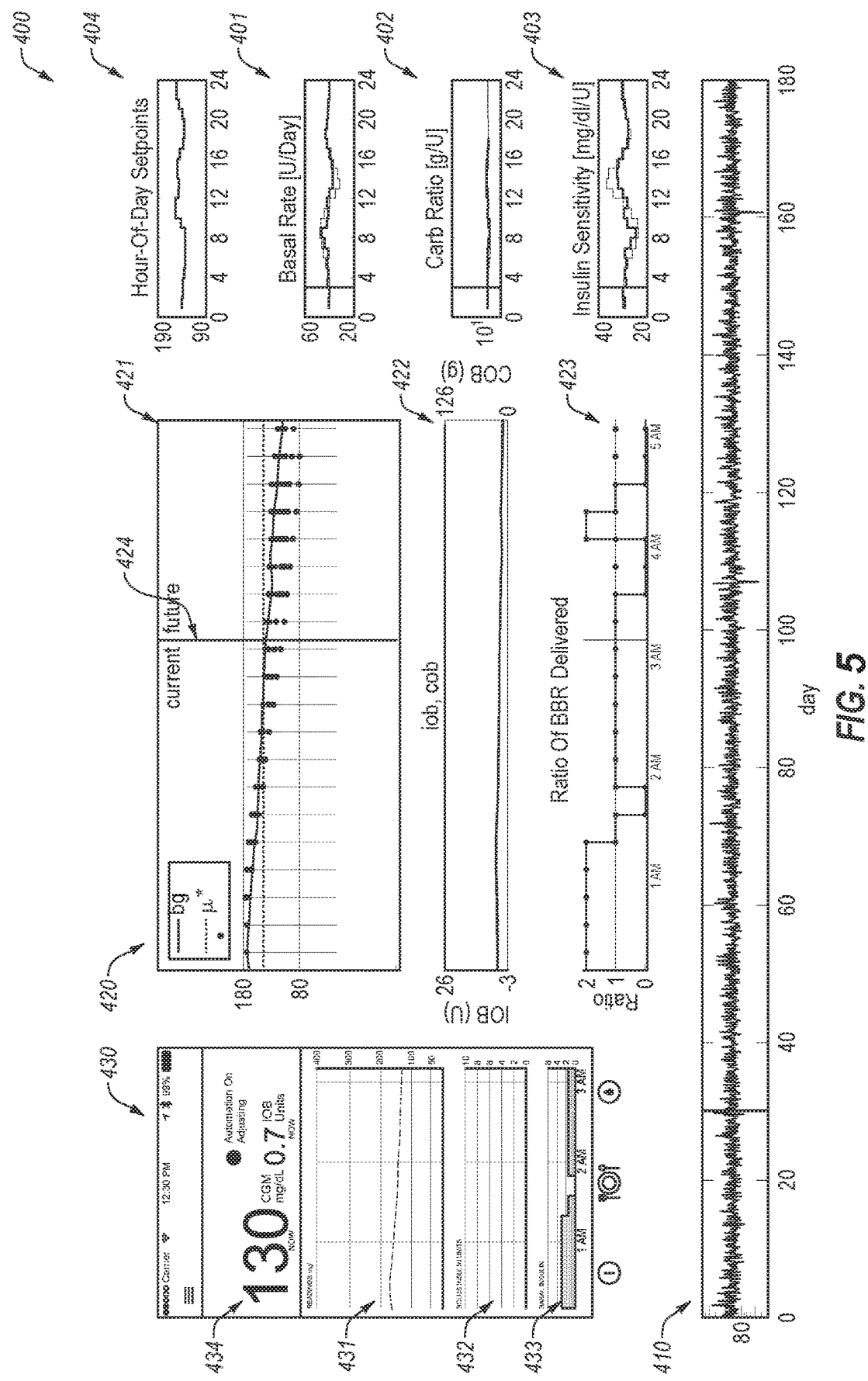
FIG. 5 illustrates data recorded for a simulated person with diabetes using methods and systems provided herein.

In some cases, FIG. 5 illustrates a simulation of a method provided herein, showing how methods and systems provided herein may generate a user interface 400 that may illustrate BBRs 401, CRs 402, ISFs 403, and blood glucose targets 404 set for multiple time blocks. For example, after a system (e.g., the system 10 of FIG. 1) has run on a PWD after thirty days, user-specific dosage parameters may be personalized based on adjustments made to the user-specific dosage parameters. For example, the user interface 400 may align the various user-specific dosage parameters over various diurnal periods throughout a day. For example, the BBR 401 may be higher around meal times (e.g., nine AM, twelve PM, and seven PM), and lower while the PWD is sleeping (e.g., eleven PM to five AM). As an additional example, the CR 402 and ISF 403 may follow a similar trajectory of variation as illustrated for the BBR 401.

In some cases, as illustrated in user interface 410 of FIG. 5, methods and/or systems of the present disclosure (including, for example, back-end computer systems) may monitor and/or track blood glucose levels over time. For example, the user interface 410 may illustrate glucose levels for one hundred and eighty days, with a bar indicating the last thirty days. In some cases, when adjusting user-specific dosage parameters, methods and systems of the present disclosure may disregard readings older than thirty days, or may weight more recent readings more heavily than older readings.

In some cases, the user interface 420 may include time aligned charts (including chart 421, chart 422, and chart 423) that can show a six hour window of the timeline illustrated in user interface 410. As illustrated in FIG. 5, chart 421 depicts the current blood glucose values as well as the predictions that have been made over time for that particular delivery time. For example, once the "current" bar 424 is reached, there may have been multiple predictions made for each time segment. As the window extends further into the future, the number of predictions may be lower. The chart 422 illustrates the calculated IOB and the calculated COB for the PWD. The chart 423 indicates whether the method or system delivered 0% of the BBR, 100% of the BBR, or 200% of the BBR for fifteen minute time segments.

As illustrated in FIG. 5, the user interface 430 depicts a possible user interface for a PWD showing some data that may be displayed on a mobile device of a PWD (e.g., the mobile computing device 60 of FIG. 1). In some cases, only the data prior to the bar 424 (e.g., historic data) may be shown in the user interface 430. In a first part 431 of the user interface 430, historic blood glucose data can be displayed. In a second section 432, announced meals and bolus insulin deliveries can be displayed. In a third section 433, the rates of basal delivery can be displayed. The third section 433 can differ from chart 423 by displaying the actual rates of basal delivery rather than a ratio of the rate delivered to the BBR. Section 434 can display a current blood glucose reading, a current IOB, and/or an indication of whether the system is automating. In some cases, more or less information can be displayed on the user interface 430 than illustrated in FIG. 5. For example, the user interface 430 may include any of the information from the user interfaces 400, 410, and/or 420 in any combination.

Additional Details about Example Pump Assembly

Figure 6A:
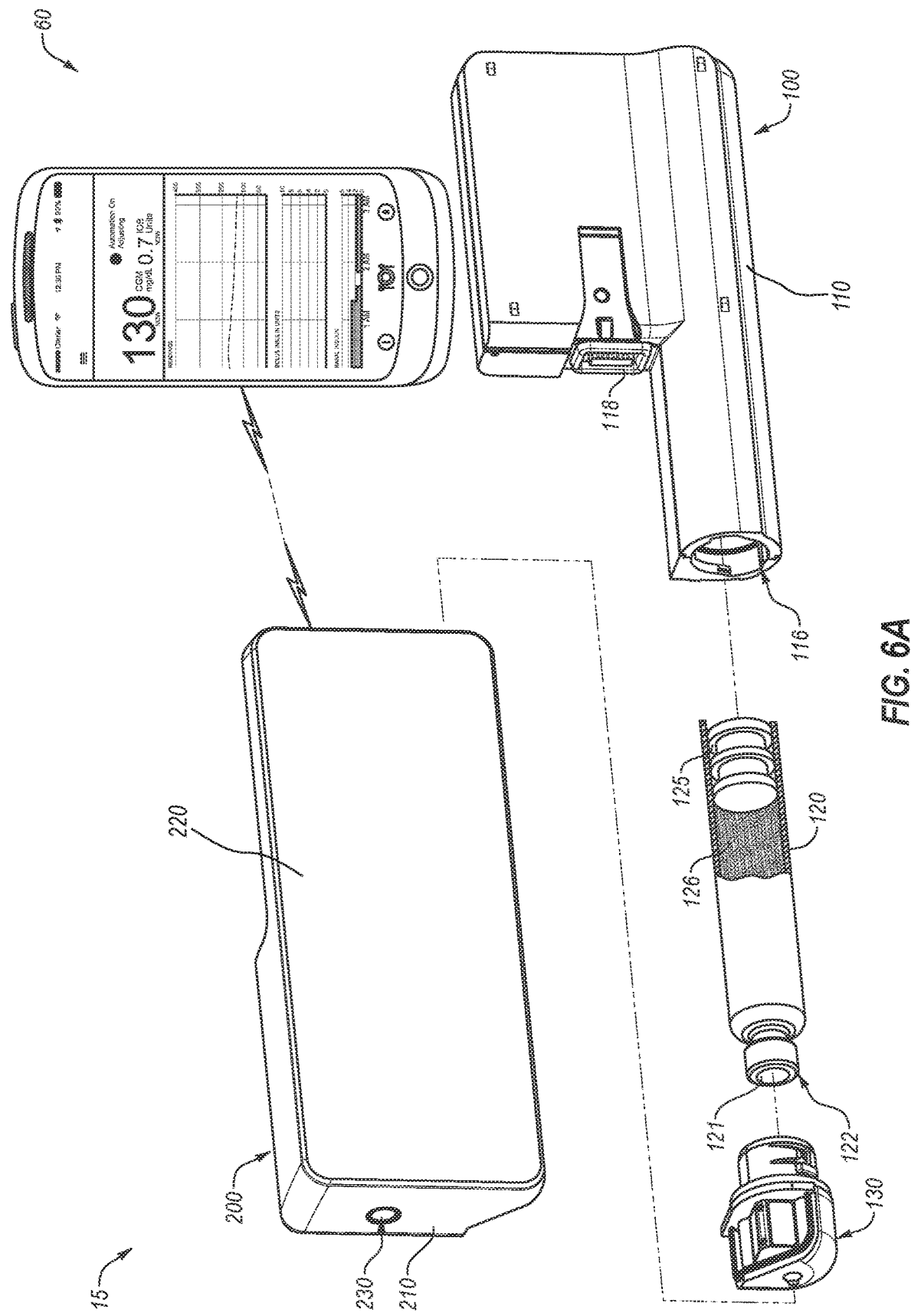
FIGS. 6A and 6B depict additional details of the example DMS of FIG. 1.
Figure 6B:
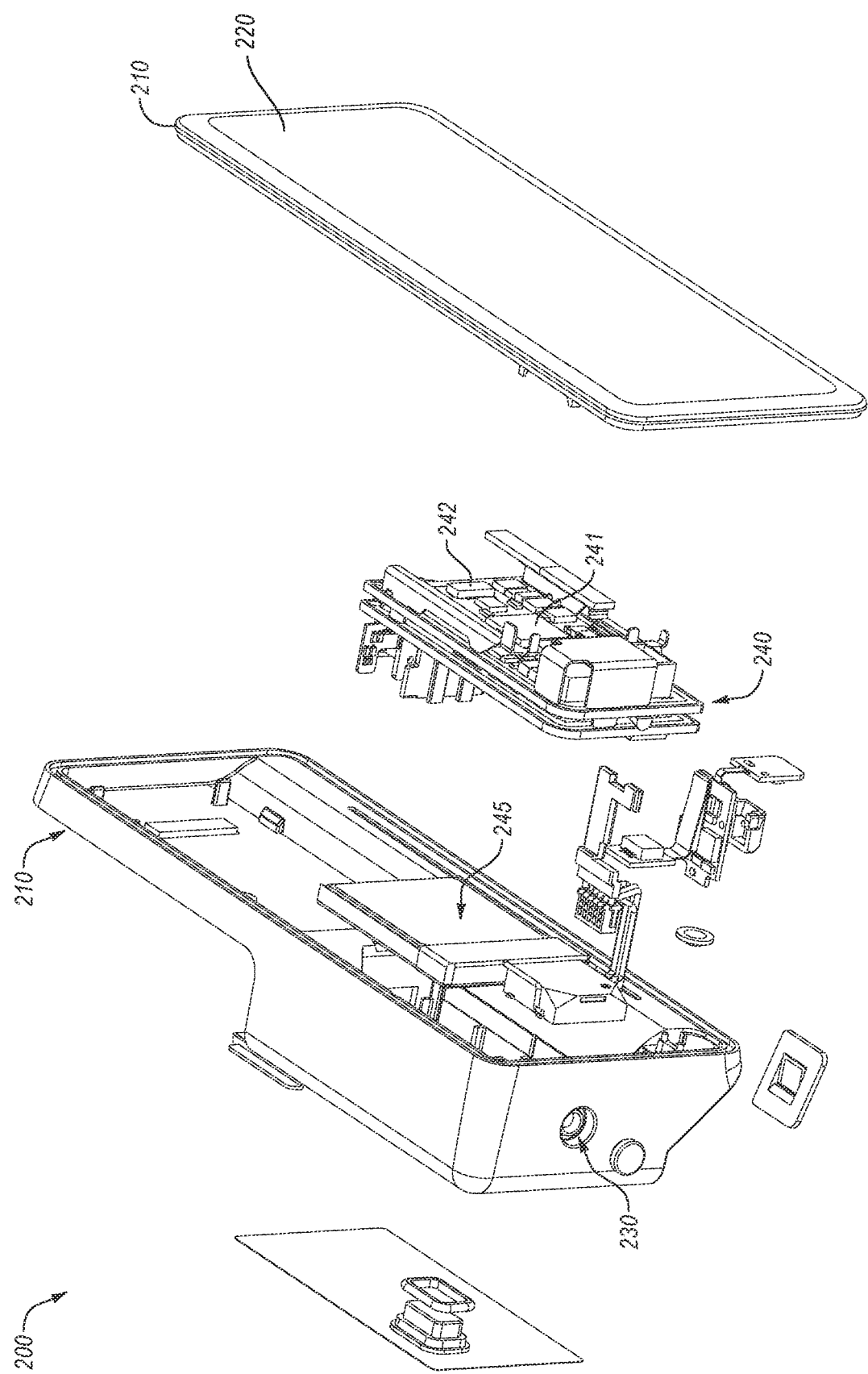

FIGS. 6A and 6B provide additional details about example pump assembly 15 as discussed above in regards to FIG. 1. FIG. 6B depicts the details of example reusable pump controller 200.

Referring now to FIG. 6A, disposable pump 100 in this embodiment includes a pump housing structure 110 that defines a cavity 116 in which a fluid cartridge 120 can be received. Disposable pump 100 also can include a cap device 130 to retain the fluid cartridge 120 in the cavity 116 of the pump housing structure 110. Disposable pump 100 can include a drive system (e.g., including a battery powered actuator, a gear system, a drive rod, and other items that are not shown in FIG. 6A) that advances a plunger 125 in the fluid cartridge 120 so as to dispense fluid therefrom. In this embodiment, reusable pump controller 200 communicates with disposable pump 100 to control the operation of the drive system. For example, in some cases, the reusable pump controller 200 can generate a message for the disposable pump 100 directing the disposable pump 100 to deliver a certain amount of insulin or deliver insulin at a certain rate. In some cases, such a message may direct the disposable pump 100 to advance the plunger 125 a certain distance. In some cases, not depicted, reusable pump controller 200 may include a user interface to control the operation of disposable pump 100. In some cases, disposable pump 100 can be disposed of after a single use. For example, disposable pump 100 can be a "one-time-use" component that is thrown away after the fluid cartridge 120 therein is exhausted. Thereafter, the user can removably attach a new disposable pump 100 (having a new fluid cartridge) to the reusable pump controller 200 for the dispensation of fluid from a new fluid cartridge. Accordingly, the user is permitted to reuse reusable pump controller 200 (which may include complex or valuable electronics, as well as a rechargeable battery) while disposing of the relatively low-cost disposable pump 100 after each use. Such a pump assembly 15 can provide enhanced user safety as a new pump device (and drive system therein) is employed with each new fluid cartridge.

The pump assembly 15 can be a medical infusion pump assembly that is configured to controllably dispense a medicine from the fluid cartridge 120. As such, the fluid cartridge 120 can contain a medicine 126 to be infused into the tissue or vasculature of a targeted individual, such as a human or animal patient. For example, disposable pump 100 can be adapted to receive a fluid cartridge 120 in the form of a carpule that is preloaded with insulin or another medicine for use in the treatment of diabetes (e.g., Exenatide (BYETTA®, BYDUREON®) and liraglutide (VICTOZA®) SYMLIN®, or others). Such a fluid cartridge 120 may be supplied, for example, by Eli Lilly and Co. of Indianapolis, Ind. The fluid cartridge 120 may have other configurations. For example, the fluid cartridge 120 may comprise a reservoir that is integral with the pump housing structure 110 (e.g., the fluid cartridge 120 can be defined by one or more walls of the pump housing structure 110 that surround a plunger to define a reservoir in which the medicine is injected or otherwise received).

In some embodiments, disposable pump 100 can include one or more structures that interfere with the removal of the fluid cartridge 120 after the fluid cartridge 120 is inserted into the cavity 116. For example, the pump housing structure 110 can include one or more retainer wings (not shown) that at least partially extend into the cavity 116 to engage a portion of the fluid cartridge 120 when the fluid cartridge 120 is installed therein. Such a configuration may facilitate the "one-time-use" feature of disposable pump 100. In some embodiments, the retainer wings can interfere with attempts to remove the fluid cartridge 120 from disposable pump 100, thus ensuring that disposable pump 100 will be discarded along with the fluid cartridge 120 after the fluid cartridge 120 is emptied, expired, or otherwise exhausted. In another example, the cap device 130 can be configured to irreversibly attach to the pump housing structure 110 so as to cover the opening of the cavity 116. For example, a head structure of the cap device 130 can be configured to turn so as to threadably engage the cap device 130 with a mating structure along an inner wall of the cavity 116, but the head structure may prevent the cap device from turning in the reverse direction so as to disengage the threads. Accordingly, disposable pump 100 can operate in a tamper-resistant and safe manner because disposable pump 100 can be designed with a predetermined life expectancy (e.g., the "one-time-use" feature in which the pump device is discarded after the fluid cartridge 120 is emptied, expired, or otherwise exhausted).

Still referring to FIG. 6A, reusable pump controller 200 can be removably attached to disposable pump 100 so that the two components are mechanically mounted to one another in a fixed relationship. In some embodiments, such a mechanical mounting can also form an electrical connection between the reusable pump controller 200 and disposable pump 100 (for example, at electrical connector 118 of disposable pump 100). For example, reusable pump controller 200 can be in electrical communication with a portion of the drive system (not shown) of disposable pump 100. In some embodiments, disposable pump 100 can include a drive system that causes controlled dispensation of the medicine or other fluid from the fluid cartridge 120. In some embodiments, the drive system incrementally advances a piston rod (not shown) longitudinally into the fluid cartridge 120 so that the fluid is forced out of an output end 122. A septum 121 at the output end 122 of the fluid cartridge 120 can be pierced to permit fluid outflow when the cap device 130 is connected to the pump housing structure 110. For example, the cap device 130 may include a penetration needle that punctures the septum 121 during attachment of the cap device 130 to the pump housing structure 110. Thus, when disposable pump 100 and reusable pump controller 200 are mechanically attached and thereby electrically connected, reusable pump controller 200 communicates electronic control signals via a hardwire-connection (e.g., electrical contacts along electrical connector 118 or the like) to the drive system or other components of disposable pump 100. In response to the electrical control signals from reusable pump controller 200, the drive system of disposable pump 100 causes medicine to incrementally dispense from the fluid cartridge 120. Power signals, such as signals from a battery (not shown) of reusable pump controller 200 and from the power source (not shown) of disposable pump 100, may also be passed between reusable pump controller 200 and disposable pump 100.

Referring again to FIGS. 1 and 5A, the pump assembly 15 can be configured to be portable and can be wearable and concealable. For example, a PWD can conveniently wear the pump assembly 15 on the PWD's skin (e.g., skin adhesive) underneath the PWD's clothing or carry disposable pump 100 in the PWD's pocket (or other portable location) while receiving the medicine dispensed from disposable pump 100. The pump assembly 15 depicted in FIG. 1 as being held in a PWD's hand 5 so as to illustrate the size of the pump assembly 15 in accordance with some embodiments. This embodiment of the pump assembly 15 is compact so that the PWD can wear the pump assembly 15 (e.g., in the PWD's pocket, connected to a belt clip, adhered to the PWD's skin, or the like) without the need for carrying and operating a separate module. In such embodiments, the cap device 130 of disposable pump 100 can be configured to mate with an infusion set 146. In general, the infusion set 146 can be a tubing system that connects the pump assembly 15 to the tissue or vasculature of the PWD (e.g., to deliver medicine into the tissue or vasculature under the PWD's skin). The infusion set 146 can include a tube 147 that is flexible and that extends from disposable pump 100 to a subcutaneous cannula 149 that may be retained by a skin adhesive patch (not shown) that secures the subcutaneous cannula 149 to the infusion site. The skin adhesive patch can retain the cannula 149 in fluid communication with the tissue or vasculature of the PWD so that the medicine dispensed through the tube 147 passes through the cannula 149 and into the PWD's body. The cap device 130 can provide fluid communication between the output end 122 (FIG. 6A) of the fluid cartridge 120 and the tube 147 of the infusion set 146. As shown in FIGS. 6A and 6B, controller housing 210 may define an opening 230 adapted to enable the tube 147 to pass through.

In some embodiments, the pump assembly 15 can be pocket-sized so that disposable pump 100 and reusable pump controller 200 can be worn in the PWD's pocket or in another portion of the PWD's clothing. In some circumstances, the PWD may desire to wear the pump assembly 15 in a more discrete manner. Accordingly, the PWD can pass the tube 147 from the pocket, under the PWD's clothing, and to the infusion site where the adhesive patch can be positioned. As such, the pump assembly 15 can be used to deliver medicine to the tissues or vasculature of the PWD in a portable, concealable, and discrete manner.

In some embodiments, the pump assembly 15 can be configured to adhere to the PWD's skin directly at the location in which the skin is penetrated for medicine infusion. For example, a rear surface of disposable pump 100 can include a skin adhesive patch so that disposable pump 100 can be physically adhered to the skin of the PWD at a particular location. In these embodiments, the cap device 130 can have a configuration in which medicine passes directly from the cap device 130 into an infusion set 146 that is penetrated into the PWD's skin. In some examples, the PWD can temporarily detach reusable pump controller 200 (while disposable pump 100 remains adhered to the skin) so as to view and interact with the user interface 220.

In some embodiments, the pump assembly 15 can operate during an automated mode to deliver basal insulin according the methods provided herein. In some cases, pump assembly 15 can operate in an open loop mode to deliver insulin at the BBR. A basal rate of insulin can be delivered in an incremental manner (e.g., dispense 0.10 U every five minutes for a rate of 1.2 U per hour) according to a selected basal insulin delivery profile. A user can use the user interface on mobile computing device 60 to select one or more bolus deliveries, for example, to offset the blood glucose effects caused by food intake, to correct for an undesirably high blood glucose level, to correct for a rapidly increasing blood glucose level, or the like. In some circumstances, the basal rate delivery pattern may remain at a substantially constant rate for a long period of time (e.g., a first basal dispensation rate for a period of hours in the morning, and a second basal dispensation rate for a period of hours in the afternoon and evening). In contrast, the bolus dosages can be more frequently dispensed based on calculations made by reusable pump controller 200 or the mobile computing device 60 (which then communicates to reusable pump controller 200). For example, reusable pump controller 200 can determine that the PWD's blood glucose level is rapidly increasing (e.g., by interpreting data received from the continuous glucose monitor 50), and can provide an alert to the user (via the user interface 220 or via the mobile computing device 60) so that the user can manually initiate the administration of a selected bolus dosage of insulin to correct for the rapid increase in blood glucose level. In one example, the user can request (via the user interface of mobile computing device 60) a calculation of a suggested bolus dosage (e.g., calculated at the mobile computing device 60 based upon information received from the user and from reusable pump controller 200, or alternatively calculated at reusable pump controller 200 and communicated back via the mobile computing device 60 for display to the user) based, at least in part, on a proposed meal that the PWD plans to consume.

Referring now to FIG. 6B, reusable pump controller 200 (shown in an exploded view) houses a number of components that can be reused with a series of successive disposable pumps 100. In particular, reusable pump controller 200 can include control circuitry 240 (e.g., a control device) and a rechargeable battery pack 245, each arranged in the controller housing 210. The rechargeable battery pack 245 may provide electrical energy to components of the control circuitry 240, other components of the controller device (e.g., a display device and other user interface components, sensors, or the like), or to components of disposable pump 100. The control circuitry 240 may be configured to communicate control or power signals to the drive system of disposable pump 100, or to receive power or feedback signals from disposable pump 100.

The control circuitry 240 of reusable pump controller 200 can include one or more microprocessors 241 configured to execute computer-readable instructions stored on one or more memory devices 242 so as to achieve any of the control operations described herein. At least one memory device 242 of the control circuitry 240 may be configured to store a number of user-specific dosage parameters. One or more user-specific dosage parameters may be input by a user via the user interface 220. Further, as described below in connection with FIG. 6A, various user-specific dosage parameters can be automatically determined and/or updated by control operations implemented by the control circuitry 240 of reusable pump controller 200. For example, the control circuitry 240 can implement a secondary feedback loop to determine and/or update one or more user-specific dosage parameters in parallel with the diabetes management system 10 operating in a closed-loop delivery mode. Whether determined automatically or received via the mobile computing device 60 (or via the user interface 220 of reusable pump controller 200), the control circuitry 240 can cause the memory device 242 to store the user-specific dosage parameters for future use during operations according to multiple delivery modes, such as closed-loop and open-loop delivery modes. Additionally, the control circuitry 240 can cause reusable pump controller 200 to periodically communicate the user-specific dosage parameters to the mobile computing device 60 for future use during operations by the mobile computing device 60 or for subsequent communication to a cloud-based computer network.

Such user-specific dosage parameters may include, but are not limited to, one or more of the following: total daily basal dosage limits (e.g., in a maximum number of units/day), various other periodic basal dosage limits (e.g., maximum basal dosage/hour, maximum basal dosage/six hour period), insulin sensitivity (e.g., in units of mg/dL/insulin unit), carbohydrate ratio (e.g., in units of g/insulin unit), insulin onset time (e.g., in units of minutes and/or seconds), insulin on board duration (e.g., in units of minutes and/or seconds), and basal rate profile (e.g., an average basal rate or one or more segments of a basal rate profile expressed in units of insulin unit/hour). Also, the control circuitry 240 can cause the memory device 242 to store (and can cause reusable pump controller 200 to periodically communicate out to the mobile computing device 60) any of the following parameters derived from the historical pump usage information: dosage logs, average total daily dose, average total basal dose per day, average total bolus dose per day, a ratio of correction bolus amount per day to food bolus amount per day, amount of correction boluses per day, a ratio of a correction bolus amount per day to the average total daily dose, a ratio of the average total basal dose to the average total bolus dose, average maximum bolus per day, and a frequency of cannula and tube primes per day. To the extent these aforementioned dosage parameters or historical parameters are not stored in the memory device 242, the control circuitry 240 can be configured to calculate any of these aforementioned dosage parameters or historical parameters from other data stored in the memory device 242 or otherwise input via communication with the mobile computing device 60.

Figure 7:
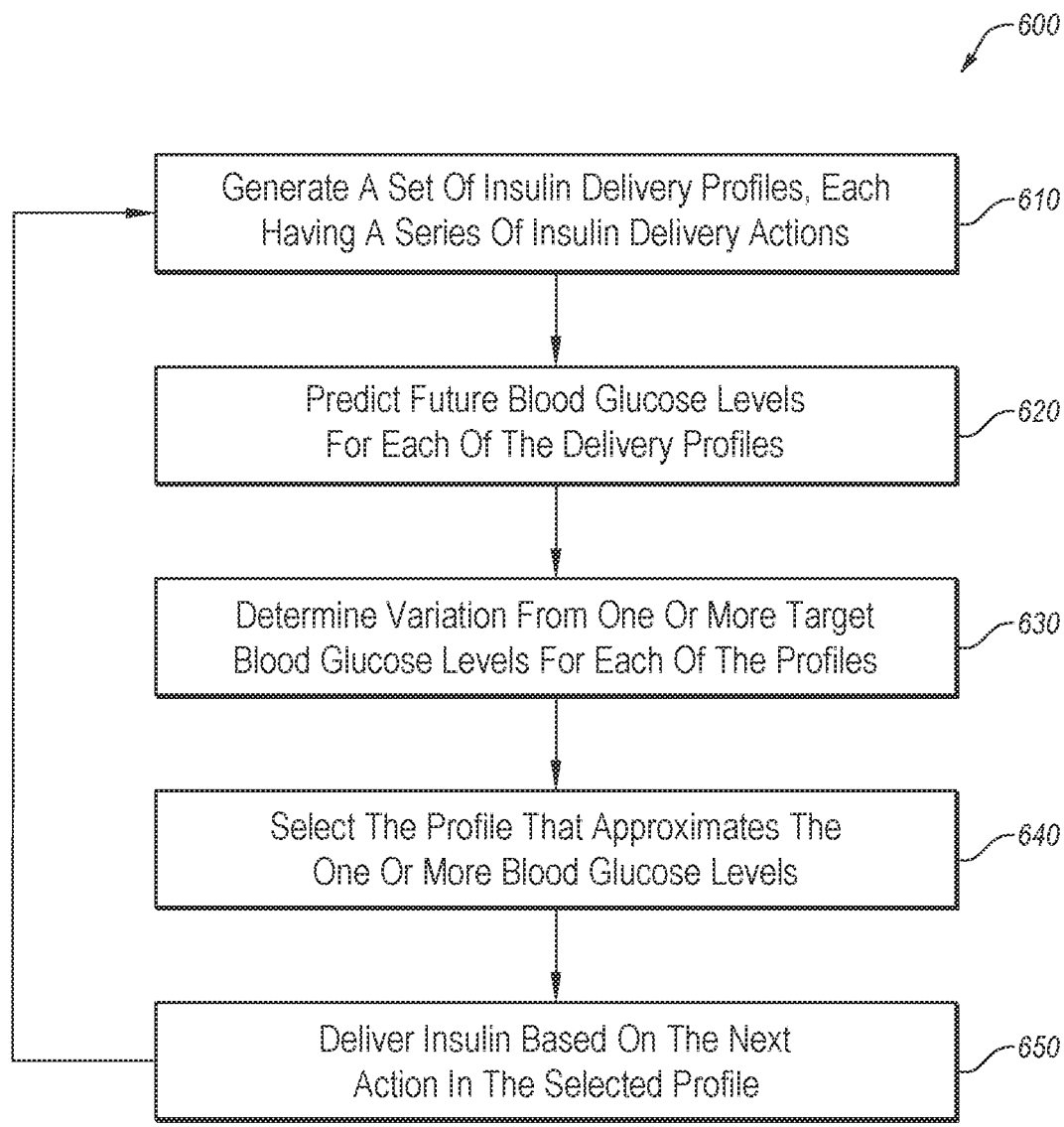
FIG. 7 illustrates a flowchart of an example method of using insulin delivery profiles.

FIG. 7 illustrates a flow diagram of an example method 600 of using insulin delivery profiles. The method 600 may be performed by any suitable system, apparatus, or device. For example, the system 10, the pump assembly 15, the mobile computing device 60 of FIG. 1, and/or a remote server may perform one or more of the operations associated with the method 600. Although illustrated with discrete blocks, the steps and operations associated with one or more of the blocks of the method 600 may be divided into additional blocks, combined into fewer blocks, or eliminated, depending on the desired implementation.

At block 610, a set of insulin delivery profiles can be generated, each having a series of insulin delivery actions. For example, the pump assembly 15 may generate a series of potential delivery actions that may include permutations based on one or more potential inflection points in the delivery actions (e.g., the permutations illustrated in the chart 300 of FIG. 3).

At block 620, a prediction can be made of future blood glucose levels for each of the delivery profiles. For example, the pump assembly 15 and/or the mobile computing device 60 of FIG. 1 can generate a prediction of future blood glucose levels at various points in time if a particular profile is followed. Such prediction may be based on the effect of glucose, insulin, carbohydrates, and/or other disturbances projected for the blood glucose levels at the various points in time.

At block 630, a determination can be made as to variations from a target blood glucose level for each of the profiles. For example, the pump assembly 15 and/or the mobile computing device 60 of FIG. 1 may compare the predicted blood glucose levels to a target blood glucose level for each of the various points in time. In some cases, the target blood glucose level may be constant and in other cases, the target blood glucose level may vary over time. In these and other cases, the variation may be measured as a distance between the target blood glucose level and the projected blood glucose level, or a square of the difference, etc. as described above.

At block 640, the profile that approximates the target blood glucose level can be selected. In some cases, the profile that minimizes variation from the target blood glucose level may be selected. For example, a cost function can be utilized and the profile with the lowest cost can be selected as the profile that approximates the target blood glucose level.

At block 650, insulin may be delivered based on the next action in the selected profile. For example, control circuitry 240 of the pump assembly 15 may send a message to the pump portion of the pump assembly 15 to deliver insulin based on the next action in the selected profile. For example, a next action may indicate that the pump is to deliver Ox, lx, or 2x of a BBR. The next action can be the first delivery action in the set of actions of the profile.

In some cases, after the block 650, the method 600 can return to the block 610 to generate another set of insulin delivery profiles, predict future blood glucose levels, determine variations from a target blood glucose level, etc. In some cases, the method 600 can be performed iteratively each time a PWD is to receive a dose of basal insulin. In these and other cases, the method 600 can routinely update delivery actions based on a repeatedly updated projection of the blood glucose levels of the PWD and the effect a particular delivery action may have on the blood glucose levels. In some cases, methods and systems provided herein can change modes if there is a lack of reliable CGM data at this point in time (e.g., the system can change modes to a mode where BBR is delivered and potentially provide notice that the system has exited the automation mode).

Modifications, additions, or omissions may be made to the method 600 without departing from the scope of the present disclosure. For example, the operations of the method 600 may be implemented in differing order. Additionally or alternatively, two or more operations may be performed at the same time. Furthermore, the outlined operations and actions are provided as examples, and some of the operations and actions may be optional, combined into fewer operations and actions, or expanded into additional operations and actions without detracting from the essence of the disclosed embodiments.

Figure 8:
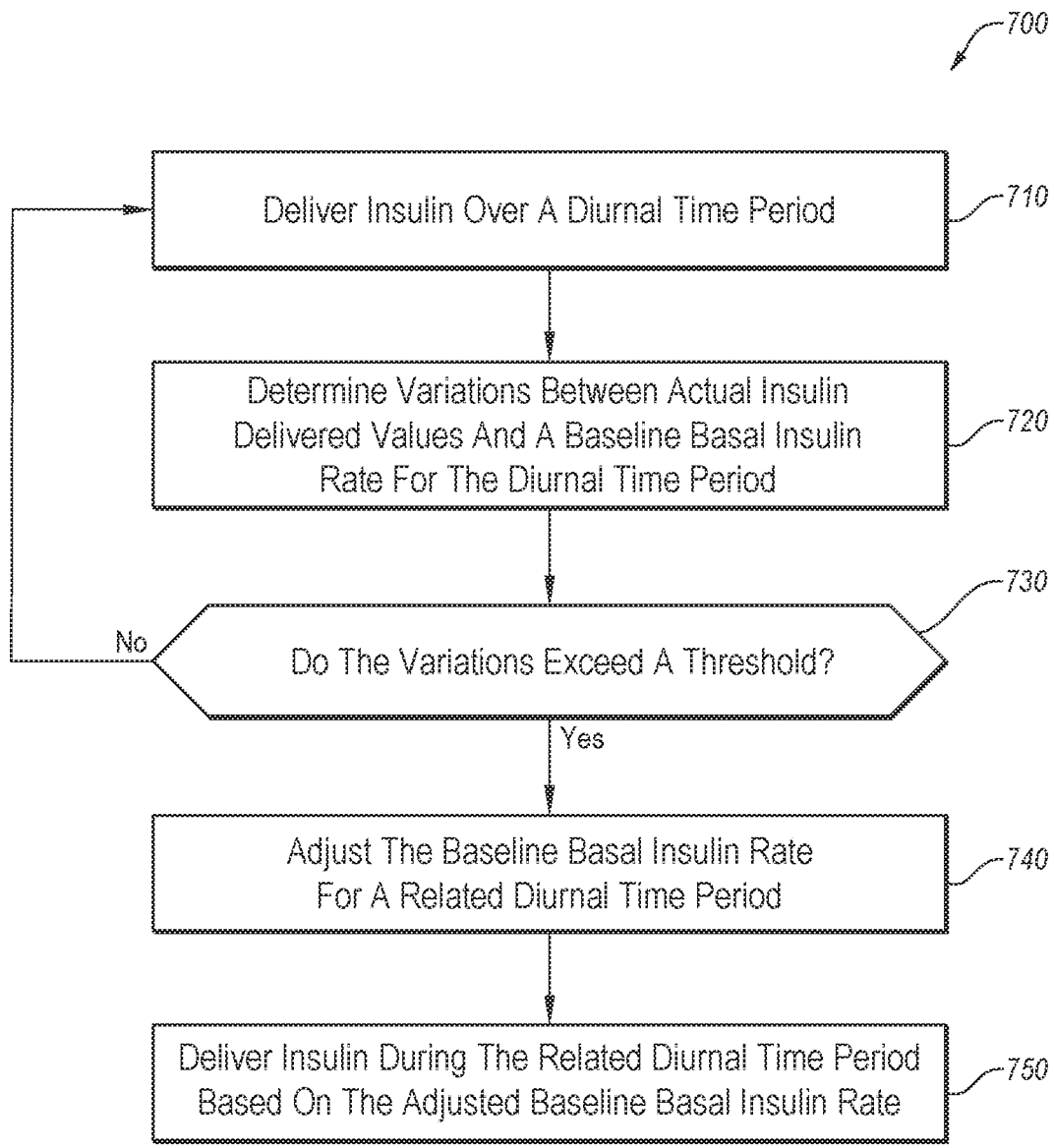
FIG. 8 illustrates a flowchart of an example method of adjusting insulin delivery rates.

FIG. 8 illustrates a flow diagram of an example method 700 of adjusting insulin delivery rates. The method 700 may be performed by any suitable system, apparatus, or device. For example, the system 10, the pump assembly 15, the mobile computing device 60 of FIG. 1, and/or a remote server may perform one or more of the operations associated with the method 700. Although illustrated with discrete blocks, the steps and operations associated with one or more of the blocks of the method 700 may be divided into additional blocks, combined into fewer blocks, or eliminated, depending on the desired implementation.

At block 710, insulin can be delivered over a diurnal time period. For example, the pump assembly 15 of FIG. 1 can deliver insulin to a PWD based on a BBR for the diurnal time period. In some cases, the insulin may be actually delivered at multiple points in time throughout the diurnal time period as a ratio of the BBR, such as 0×, 1×, and 2×.

At block 720, variations between actual insulin delivered values and the BBR for the diurnal time period can be determined. For example, if the delivery actions throughout the diurnal time period deliver a ratio of the BBR, the actual delivery actions may be averaged over the diurnal time period to find an average ratio for the diurnal time period. In these and other cases, the actual insulin delivered values can be based on periodically projected blood glucose levels and the BBR. For example, a set of insulin delivery profiles can be generated and a delivery action selected as described in the present disclosure (e.g., as described in FIG. 7).

At block 730, a determination is made as to whether the variations between the actual insulin delivered values and the baseline basal insulin rate exceeds a threshold. If the variations do exceed the threshold, the method 700 may proceed to the block 740. If the variations do not exceed the threshold, the method 700 may proceed back to the block 710. In some cases, the threshold may be based on a ratio of the baseline basal delivery rate. For example, the threshold may include that the average rate over the diurnal period be above 150% of the BBR or below 50% of the BBR for the actual delivery values over the diurnal time period.

At block 740, the baseline basal insulin rate can be adjusted for a related diurnal time period. For example, the BBR can be adjusted higher by a certain amount (e.g., 1%, 2%, or 5%) if the variations went above a threshold and can be adjusted lower by a certain amount (e.g., 1%, 2%, or 5%) if the variations went below a threshold. In some cases, the related diurnal time period can be the same block of time (e.g., if the variations exceeded the threshold during the 2 PM to 3 PM diurnal period, then the BBR from 2 PM to 3 PM of the next day may be adjusted) on another day in the future, and in some cases, the related diurnal time period can be a different time on another day (e.g., if the variations exceeded the threshold during the 2 PM to 3 PM diurnal period, then the BBR from 1 PM to 2 PM of the next day may be adjusted). In some cases, such an adjustment may be performed once per day for all the diurnal periods of that day.

In some cases, the adjustment at block 740 can include smoothing of the adjustment. For example, a potential modification can be compared to the BBR of the preceding diurnal time period or the following diurnal time period, and may modify the adjustment to be closer to the other diurnal time periods. Additionally or alternatively, the BBR can be smoothed by comparing the potential modification to BBRs of the same time of day for preceding days to determine whether the potential modification may be responsive to an unusual day.

In some cases, the adjustment at block 740 can consider other factors. For example, the adjustment can be based on penalizing a modification that increases the probability of the PWD having a hypoglycemic event (e.g., by penalizing modifications that may increase the probability of the blood glucose levels of the PWD falling below a threshold low blood glucose level). In these and other cases, in addition to or in place of adjusting the BBR, other user-specific dosage-guidelines can be adjusted. For example, ISF and CR can also be adjusted according to the present disclosure. In some cases, if BBR is adjusted higher, ISF may be adjusted higher by the same or an approximately proportional percentage amount and CR may be adjusted lower by the same or an approximately proportional percentage amount of the BBR.

At block 750, insulin may be delivered during the related diurnal time period based on the adjusted baseline basal insulin rate. For example, the insulin pump can deliver insulin based on the adjusted baseline basal insulin rate. In some cases, such delivery can include a control device (e.g., the control circuitry 240 of FIG. 6B) sending a message to the insulin pump to deliver insulin.

Modifications, additions, or omissions may be made to the method 700 without departing from the scope of the present disclosure. For example, the operations of the method 700 may be implemented in differing order. Additionally or alternatively, two or more operations may be performed at the same time. Furthermore, the outlined operations and actions are provided as examples, and some of the operations and actions may be optional, combined into fewer operations and actions, or expanded into additional operations and actions without detracting from the essence of the disclosed embodiments.

Figure 9:
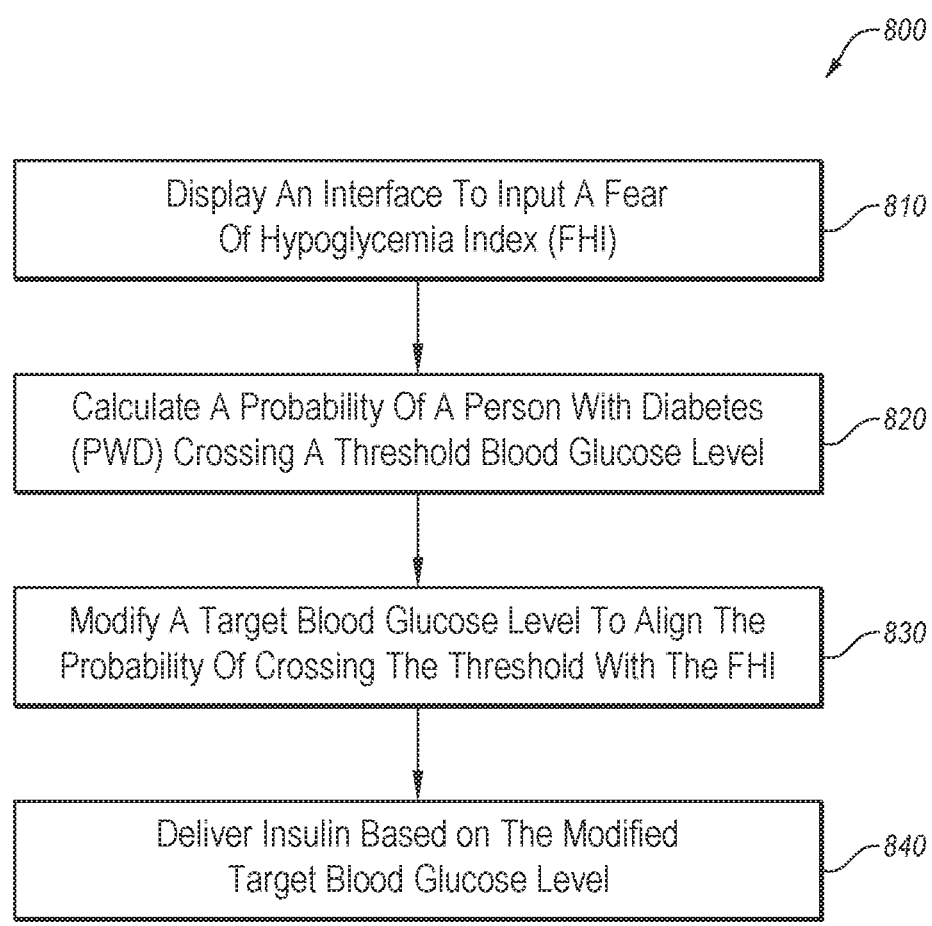
FIG. 9 illustrates a flowchart of an example method of utilizing a fear of hypoglycemia index.

FIG. 9 illustrates a flowchart of an example method 800 of utilizing a fear of hypoglycemia index. The method 800 may be performed by any suitable system, apparatus, or device. For example, the system 10, the pump assembly 15, the mobile computing device 60 of FIG. 1, and/or a remote server may perform one or more of the operations associated with the method 800. Although illustrated with discrete blocks, the steps and operations associated with one or more of the blocks of the method 800 may be divided into additional blocks, combined into fewer blocks, or eliminated, depending on the desired implementation.

At block 810, an interface can be displayed to a user to input an FHI. For example, an interface can be displayed on a mobile computing device (e.g., the mobile computing device 60 of FIG. 1) and/or to a terminal connected over a network such as the internet to a remote server. In some cases, the user (e.g., a PWD or a healthcare professional) can be presented with an interactive feature from which the user can select the FHI. In these and other cases, the interface can include a variety of ways that the user can input the FHI, such as a preferred blood glucose level, a preferred probability of going above or below a certain threshold, a textual description of a blood glucose level (e.g., "prefer high"), etc. In these and other cases, the FHI can correspond to a threshold blood glucose level and an acceptable probability of crossing the threshold blood glucose level. For example, "prefer high" may designate a low threshold blood glucose level as 100 mg/dl, with a target blood glucose level of 150 mg/dl, and a high threshold blood glucose level of 220 mg/dl, and an acceptable probability of 5% for exceeding either the low or the high threshold values.

At block 820, a probability of a PWD crossing a threshold blood glucose level is calculated. For example, a calculation can be made as to how likely the PWD is to cross the threshold blood glucose level corresponding to the FHI. In these and other cases, the probability of crossing the threshold can also be compared to the acceptable probability of crossing the threshold. For example, if the FHI indicates that a 5% probability of exceeding a threshold is acceptable, the calculated probability of exceeding the threshold can be compared to the 5% acceptable probability.

At block 830, target blood glucose level can be modified to more closely align the probability of crossing the threshold with the FHI. For example, if the probability of dropping below a threshold is higher than the acceptable probability, the target blood glucose level may be adjusted higher such that the probability is closer to the acceptable probability. In some cases, the target blood glucose level can be adjusted such that the probability of crossing the threshold is the same as the acceptable probability. In these and other cases, the modification of the baseline basal insulin rate can also be based on the actual insulin delivered compared to the BBR for a diurnal period. For example, if four delivery actions occur during a diurnal time period and each of them deliver 2× the BBR, the BBR can be modified based on both the FHI and the 2× delivered. Continuing the example, if a user had selected a low FHI (e.g., the PWD is not as concerned about going low), the target blood glucose level can be changed by a large amount (e.g., between 0% and 5%) while if the user had selected a high FHI (e.g., the PWD is concerned about going low), the BBR can be changed be a smaller amount (e.g., between 0% and 2%). In these and other cases, the change amount can vary depending on whether it is adjusting up or down. For example, for a PWD that prefers high blood glucose levels, methods and systems of the present disclosure can use a larger change when adjusting the BBR upwards and a lower change when adjusting the BBR downwards. In some cases, increases to the target blood glucose level can be unconstrained, but decreases constrained to 5% or less, 3% or less, 2% or less, or 1% or less.

At block 840, insulin can be delivered based on the modified target blood glucose level. For example, a control device can determine insulin delivery profiles or rates based the target blood glucose level(s) using any suitable method, including the methods described above. In some cases, the delivery of insulin can be based off of one or more insulin delivery profiles that can be generated, and selecting one of the profiles that most closely approximates a target blood glucose level. In these and other cases, the actions of the delivery profiles can be a ratio of the modified BBR. For example, the delivery actions can include one of delivering 0x, 1x, or 2x the modified BBR.

In some cases, the delivery actions of the delivery profiles can be based off of the FHI as well. For example, for a first FHI (e.g., the PWD is concerned about going low), the possible ratios used in the delivery actions of the profile can include 0x, 0.5x, 1x and 1.5x the BBR (e.g., for a PWD that prefers low), while for a second FHI, the possible ratios used in the delivery actions of the profile can include 0x, 1x, 2x, and 3x (e.g., for a PWD that prefers high).

Modifications, additions, or omissions may be made to the method 800 without departing from the scope of the present disclosure. For example, the operations of the method 800 may be implemented in differing order. Additionally or alternatively, two or more operations may be performed at the same time. Furthermore, the outlined operations and actions are provided as examples, and some of the operations and actions may be optional, combined into fewer operations and actions, or expanded into additional operations and actions without detracting from the essence of the disclosed embodiments.

Figure 10:
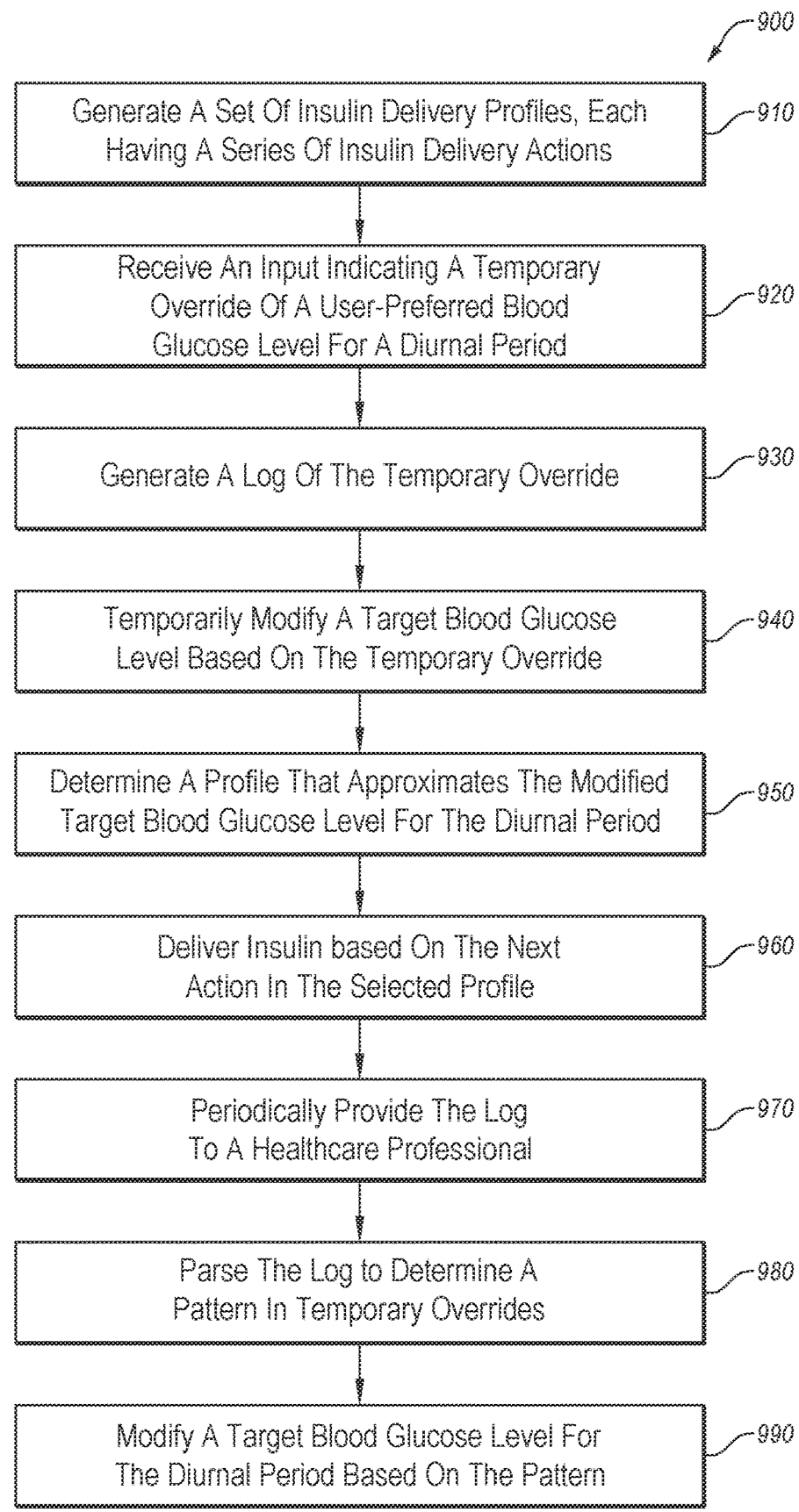
FIG. 10 illustrates a flowchart of an example method of utilizing a temporary override.

FIG. 10 illustrates a flowchart of an example method 900 of utilizing a temporary override. The method 900 may be performed by any suitable system, apparatus, or device. For example, the system 10, the pump assembly 15, the mobile computing device 60 of FIG. 1, and/or a remote server may perform one or more of the operations associated with the method 900. Although illustrated with discrete blocks, the steps and operations associated with one or more of the blocks of the method 900 may be divided into additional blocks, combined into fewer blocks, or eliminated, depending on the desired implementation.

At block 910, a set of insulin delivery profiles may be generated, each having a series of insulin delivery actions. For example, an electronic device (e.g., the pump assembly 15, the mobile computing device 60 of FIG. 1 and/or a remote server) may generate a set of profiles in accordance with the present disclosure.

At block 920, an input indicating a temporary override may be received. The temporary override can indicate a user-preferred blood glucose level for one or more diurnal periods. For example, a user (e.g., a PWD) may be presented with a field or other entry component where the user can enter a numerical blood glucose level for a set period of time. As another example, the user may be presented with multiple activities (e.g., exercising, driving a car for an extended period of time, etc.) and when the activity will be performed. As another example, the user may be presented with a series of textual descriptions of preferred blood glucose levels (e.g., "do not go low," or "do not go high"). In these and other cases, the user may be limited in selecting a temporary override for a period of time some point in the future (e.g., at least thirty minutes in the future).

At block 930, a log of the temporary override can be generated. For example, the electronic device can record what was selected for the temporary override (e.g., a target blood glucose level, a particular activity, etc.), when, and/or for how long. In some cases, the log may be updated each time the user inputs a temporary override.

At block 940, a baseline basal insulin rate (BBR) can be temporarily modified based on the temporary override. For example, the BBR can be modified to more closely align the BBR with the user-preferred blood glucose level. For example, the BBR can be adjusted higher if the temporary override indicates a lower than normal blood glucose level. As another example, the BBR can be adjusted lower if the temporary override indicates a higher than normal blood glucose level. In some cases, the temporary override from the block 920 can be received and the BBR can be modified prior to generating the set of profiles, or the set of profiles can be updated after the temporary override is received and/or the BBR is modified.

At block 950, a determination can be made as to which profile from the set of profiles approximates the user-preferred blood glucose level during the diurnal period. For example, a predicted blood glucose level for various points in time can be projected based on each of the profiles. The variation from the user-preferred blood glucose level can be analyzed, for example, by accumulating the variation over time and finding the profile with the lowest variation from the user-preferred blood glucose level. In these and other cases, the profile that most closely approximates the user-preferred blood glucose level can be selected as the basis for delivery actions of insulin.

At block 960, insulin can be delivered based on the next action in the selected profile. For example, a given profile that was selected might have sixteen delivery actions spanning four hours, and the first of sixteen actions may be taken to deliver insulin. In some cases, the block 960 can include control circuitry or another control device generating a message to be provided to a pump to deliver insulin in accordance with the next action in the selected profile.

At block 970, the log can be periodically provided to a healthcare professional. For example, the log generated and/or updated at block 930 can be sent to a healthcare professional using email, text message, via an app, etc., such that the healthcare professional can review the overrides that have occurred for a PWD.

At block 980, the log can be parsed to determine if a pattern is present in the temporary overrides. For example, the PWD may input a temporary override every Monday, Wednesday, and Friday from 6 PM to 7 PM when they exercise. As another example, the PWD may input a temporary override Monday through Friday from 5:30 PM until 6:15 PM while the PWD drives home from work. The log can be parsed to find such patterns of overrides.

At block 990, the baseline basal insulin rate can be modified for a given diurnal period based on the pattern. Following the first example given above at block 980, methods and systems of the present disclosure can adjust the BBR for 6 PM to 7 PM on Monday, Wednesday and Friday based on the repeated overrides occurring at those times. Following the second example given above at block 980, methods and systems of the present disclosure can adjust the BBR from 5:30 PM to 6:15 PM Monday through Friday based on the repeated overrides for that span of time.

Modifications, additions, or omissions may be made to the method 900 without departing from the scope of the present disclosure. For example, the operations of the method 900 may be implemented in differing order (e.g., the block 920 can be performed after the block 910, and/or the blocks 970 and/or 980 can be performed any time after the block 930). Additionally or alternatively, two or more operations may be performed at the same time. Furthermore, the outlined operations and actions are provided as examples, and some of the operations and actions may be optional (e.g., the blocks 930, 940, 970, 980, and/or 990), combined into fewer operations and actions, or expanded into additional operations and actions without detracting from the essence of the disclosed embodiments.

The embodiments described herein may include the use of a special-purpose or general-purpose computer including various computer hardware or software modules, as discussed in greater detail below.

Embodiments described herein may be implemented using computer-readable media for carrying or having computer-executable instructions or data structures stored thereon. Such computer-readable media may be any available media that may be accessed by a general-purpose or special-purpose computer. By way of example, and not limitation, such computer-readable media may include non-transitory computer-readable storage media including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage medium which may be used to carry or store desired program code in the form of computer-executable instructions or data structures and which may be accessed by a general-purpose or special-purpose computer. Combinations of the above may also be included within the scope of computer-readable media.

Computer-executable instructions comprise, for example, instructions and data which cause a general-purpose computer, special-purpose computer, or special-purpose processing device (e.g., one or more processors) to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the terms "module" or "component" may refer to specific hardware implementations configured to perform the operations of the module or component and/or software objects or software routines that may be stored on and/or executed by general-purpose hardware (e.g., computer-readable media, processing devices, etc.) of the computing system. In some embodiments, the different components, modules, engines, and services described herein may be implemented as objects or processes that execute on the computing system (e.g., as separate threads). While some of the systems and methods described herein are generally described as being implemented in software (stored on and/or executed by general-purpose hardware), specific hardware implementations or a combination of software and specific hardware implementations are also possible and contemplated. In the present description, a "computing entity" may be any computing system as previously defined herein, or any module or combination of modulates running on a computing system.

Any ranges expressed herein (including in the claims) are considered to be given their broadest possible interpretation. For example, unless explicitly mentioned otherwise, ranges are to include their end points (e.g., a range of "between X and Y" would include X and Y). Additionally, ranges described using the terms "approximately" or "about" are to be understood to be given their broadest meaning consistent with the understanding of those skilled in the art. Additionally, the term approximately includes anything within 10%, or 5%, or within manufacturing or typical tolerances.

All examples and conditional language recited herein are intended for pedagogical objects to aid the reader in understanding the disclosure and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the disclosure.

What is claimed is:

1. A method of providing insulin delivery instructions for an insulin delivery device, the method comprising:
   receiving one or more user-specific dosage parameters;
   responsive to the one or more user-specific dosage parameters, generating a plurality of user-specific basal delivery profile permutations, each user-specific basal delivery profile permutation having an intended basal rate and an intended delivery time duration for the intended basal rate;
   selecting a first user-specific basal delivery profile permutation from the plurality of user-specific basal delivery profile permutations;
   generating the insulin delivery instructions comprising the intended basal rate of the first user-specific basal delivery profile permutation and a variable delivery time duration relative to the intended delivery time duration of the first user-specific basal delivery profile permutation; and
   providing the generated insulin delivery instructions to the insulin delivery device.

2. The method of claim 1, further comprising:
   receiving blood glucose level data of a user according to a blood glucose level testing schedule;
   responsive to the received blood glucose level data from the user, selecting a second user-specific basal delivery profile permutation from the plurality of user-specific basal delivery profile permutations;
   generating updated insulin delivery instructions comprising the intended basal rate of the second user-specific basal delivery profile permutation and a second variable delivery time duration relative to the intended delivery time duration of the second user-specific basal delivery profile permutation; and
   providing the generated updated insulin delivery instructions to the insulin delivery device.

3. The method of claim 1, wherein the variable delivery time duration is less than the intended delivery time duration of the first user-specific basal delivery profile permutation.

4. The method of claim 1, wherein the variable delivery time duration is less than the intended delivery time duration of the first user-specific basal delivery profile permutation by one or more hours or by less than sixty minutes.

5. The method of claim 1, further comprising:
   responsive to a loss of receiving up-to-date blood glucose data according to a blood glucose level testing schedule and a passage of the variable delivery time duration, generating adjusted insulin delivery instructions comprising an adjusted basal rate; and
   providing the adjusted insulin delivery instructions to the insulin delivery device.

6. The method of claim 5, wherein the adjusted insulin delivery instructions comprise a generic basal rate determined based on the received one or more user-specific dosage parameters.

7. The method of claim 1, wherein receiving one or more user-specific dosage parameters comprises receiving the one or more user-specific dosage parameters at a device remote to the insulin delivery device.

8. The method of claim 1, wherein receiving one or more user-specific dosage parameters comprises receiving the one or more user-specific dosage parameters via wireless communication.

9. The method of claim 1, wherein each of the plurality of user-specific basal delivery profile permutations comprises a projected effect of the respective user-specific basal delivery profile permutations on a blood glucose level of a user.

10. A system comprising:
    a blood glucose monitor;
    an insulin delivery device;
    a controller remote from the blood glucose monitor and the insulin delivery device, the controller configured to:
       receive one or more user-specific dosage parameters;
       responsive to the one or more user-specific dosage parameters, generating a plurality of user-specific basal delivery profile permutations, each user-specific basal delivery profile permutation having an intended basal rate and intended delivery time duration for the intended basal rate;
       selecting a first user-specific basal delivery profile permutation from the plurality of user-specific basal delivery profile permutations;
       generating insulin delivery instructions comprising the intended basal rate of the first user-specific basal delivery profile permutation and a variable delivery time duration relative to the intended delivery time duration of the first user-specific basal delivery profile permutation; and
       transmitting the generated insulin delivery instructions to the insulin delivery device.

11. The system of claim 10, wherein the controller further configured to:
    receive, from the blood glucose monitor, blood glucose level data of a user according to a blood glucose level testing schedule;
    responsive to the received blood glucose level data the blood glucose monitor, select a second user-specific basal delivery profile permutation from the plurality of user-specific basal delivery profile permutations;
    generate updated insulin delivery instructions comprising the intended basal rate of the second user-specific basal delivery profile permutation and a second variable delivery time duration relative to the intended delivery time duration of the second user-specific basal delivery profile permutation; and
    transmit the generated updated insulin delivery instructions to the insulin delivery device.

12. The system of claim 10, wherein the variable delivery time duration is less than the intended delivery time duration of the first user-specific basal delivery profile permutation.

13. The system of claim 10, wherein the variable delivery time duration is less than the intended delivery time duration of the first user-specific basal delivery profile permutation by one or more hours or by less than sixty minutes.

14. The system of claim 10, wherein the controller further configured to:
    responsive to a loss of receiving up-to-date blood glucose data from the blood glucose monitor according to a blood glucose level testing schedule and a passage of the variable delivery time duration, generate adjusted insulin delivery instructions comprising an adjusted basal rate; and
    transmit the adjusted insulin delivery instructions to the insulin delivery device.

15. The system of claim 14, wherein the adjusted insulin delivery instructions comprise a generic basal rate determined based on the received one or more user-specific dosage parameters.

16. The system of claim 10, wherein each of the plurality of user-specific basal delivery profile permutations comprises a projected effect of the respective user specific basal delivery profile permutations on a blood glucose level of a user.

17. A system comprising:
   an insulin delivery device;
   a controller remote from the insulin delivery device and configured to control at least portions of an operation of the insulin delivery device, the controller configured to:
      generate a plurality of user-specific basal delivery profile permutations, each user-specific basal delivery profile permutation having an intended basal rate and an intended delivery time duration for the intended basal rate, wherein each of the plurality of user-specific basal delivery profile permutations comprises a projected effect of the respective user-specific basal delivery profile permutation on a blood glucose level of a user due to the intended delivery time duration and the intended base rate;
      responsive to blood glucose data, select a first user-specific basal delivery profile permutation from the plurality of user-specific basal delivery profile permutations;
      generate insulin delivery instructions comprising the intended basal rate of the first user-specific basal delivery profile permutation and a variable delivery time duration relative to the intended delivery time duration of the first user-specific basal delivery profile permutation; and
      transmit the generated insulin delivery instructions to the insulin delivery device to cause the insulin delivery device to deliver insulin to a user according to the generated insulin delivery instructions.

18. The system of claim 17, wherein the insulin delivery device is configured to revert to an initial baseline basal delivery rate upon passage of the variable delivery time duration absent new insulin delivery instructions from the controller.

19. The system of claim 17, wherein the variable delivery time duration is less than the intended delivery time duration of the first user-specific basal delivery profile permutation.

20. The system of claim 17, wherein the variable delivery time duration is less than the intended delivery time duration of the first user-specific basal delivery profile permutation by one or more hours or by less than sixty minutes.

* * * * *

UNITED STATES PATENT AND TRADEMARK OFFICE
CERTIFICATE OF CORRECTION

PATENT NO. : 11,147,921 B2  
APPLICATION NO. : 16/393831  
DATED : October 19, 2021  
INVENTOR(S) : Lane Desborough and Bryan Mazlish Page 1 of 1

It is certified that error appears in the above-identified patent and that said Letters Patent is hereby corrected as shown below:

In the Specification

| | | |
|---|---|---|
| Column 1, | Line 8, | change "2019 the disclosure" to --2019, the disclosure-- |
| Column 3, | Line 7, | change "Ox and 3$x$" to --0$x$ and 3$x$-- |
| Column 3, | Line 12, | change "at Ox baseline" to --at 0$x$ baseline-- |
| Column 5, | Line 8, | change "at Ox the" to --at 0$x$ the-- |
| Column 6, | Line 55, | change "Ox, 1x, or" to --0$x$, 1$x$, or-- |
| Column 29, | Line 59, | change "for Bat into" to --for $BG_{it}$ into-- |
| Column 42, | Line 62, | change "deliver Ox, 1x," to --deliver 0$x$, 1$x$,-- |
| Column 46, | Line 2, | change "Ox, 1x, or" to --0$x$, 1$x$, or-- |
| Column 46, | Line 7, | change "Ox, 0.5x, 1x" to --0x, 0.5x, 1x-- |
| Column 46, | Line 9, | change "Ox, 0.5x, 1x" to --0x, 1x, 2x-- |

Signed and Sealed this  
Twenty-ninth Day of March, 2022

Drew Hirshfeld  
*Performing the Functions and Duties of the*  
*Under Secretary of Commerce for Intellectual Property and*  
*Director of the United States Patent and Trademark Office*